(12) United States Patent
Kong et al.

(10) Patent No.: US 8,241,898 B2
(45) Date of Patent: Aug. 14, 2012

(54) REGENERATIVE DOT CELLS

(75) Inventors: Wuyi Kong, San Jose, CA (US);
Shaowei Li, Mountain View, CA (US);
Peter Lorenz, Belmont, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 214 days.

(21) Appl. No.: 12/316,332

(22) Filed: Dec. 10, 2008

(65) Prior Publication Data
US 2009/0155226 A1 Jun. 18, 2009

Related U.S. Application Data

(60) Provisional application No. 61/007,221, filed on Dec. 10, 2007.

(51) Int. Cl.
*C12N 5/00* (2006.01)
(52) U.S. Cl. ...................................... 435/325
(58) Field of Classification Search ............... 435/325
See application file for complete search history.

(56) References Cited

U.S. PATENT DOCUMENTS

| | | |
|---|---|---|
| 2003/0032184 A1 | 2/2003 | Lagasse et al. |
| 2006/0239983 A1 | 10/2006 | Anversa |

FOREIGN PATENT DOCUMENTS

| | | |
|---|---|---|
| WO | 97/25995 | 7/1997 |
| WO | 2007/062198 | 5/2007 |

OTHER PUBLICATIONS

Adzick; et al., "Cells, Matrix, Growth Factors, and the Surgeon", Annals of Surgery (1994) 220(1):10-18.
Alverez-Dolado; et al., "Cortical Inhibition Modified by Embryonic Neural Precursors Grafted into the Postnatal Brain", The Journal of Neuroscience, Jul. 12, 2006, 26(28):7380-7389.
D'Ippolito; et al., "Marrow-isolated adult multilineage inducible (MIAMI) cells, a unique population of postnatal young and old human cells with extensive expansion and differentiation potential", Journal of Cell Science (2004), 117:2971-2981.
Eisenberg; et al., "Bone Marrow Cells Transdifferentiate to Cardiomyocytes When Introduced into the Embryonic Heart", Stem Cells (2006), 24:1236-1245.
Fougerousse; et al., "Human-mouse differences in the embryonic expression patterns of development control genes and disease genes", Human Molecular Genetics (2000), 9(2):165-173.
Holden, "Controversial Marrow Cells Coming Into Their Own", Science, Feb. 9, 2007, 315:760-761.
Iino; et al, "Single Molecule Imaging of Green Fluorescent Proteins in Living Cells: E-Cadherin Forms Oligomers on the Free Cell Surface", Biophysical Journal (2001), 80:2667-2677.
Jang; et al., "Hematopoietic stem cells convert into liver cells within days without fusion", Nature Cell Biology, Jun. 2004, 6(6):532-539.
Jiang; et al., "Pluripotency of mesenchymal stem cells derived from adult marrow", Nature, Jul. 4, 2002, 418:41-49.
Kogler; et al., "A New Human Somatic Stem Cell from Placental Cord Blood with Intrinsic Pluripotent Differentiation Potential", The Journal of Experimental Medicine (2004), 200:123-135.
Medina; et al., "Isolation of Epithelial Stem Cells From Dermis by a Three-Dimensional Culture System" Journal of Cellular Biochemistry (2006), 98:174-184.
Newsome; et al., "Basic-Liver, Pancreas, and Biliary Tract", Gastroenterology (2003), 124:1891-1900.
Nygren; et al., "Bone marrow-derived hematopoietic cells generate cardiomyocytes at a low frequency through cell fusion but not transdifferentiation", Nature Medicine (2004), 10(5):494-501.
Petersen; et al., "Bone Marrow as a Potential Source of Hepatic Oval Cells", Science (1999), 284:1168-1170.
Rizvi; et al., "Bone marrow-derived cells fuse with normal and transformed intestinal stem cells", PNAS, Apr. 18, 2006, 103(16):6321-6325.
Roybon; et al., "Failure to Transdifferentiation of Adult Hematopoietic Stem Cells into Neurons", Stem Cells (2006), 24:1594-1604.
Sasaki; et al., "Mesenchymal Stem Cells Are Recruited into Wounded Skin and Contribute to Wound Repair by Transdifferentiation into Multiple Skin Cell Type", The Journal of Immunology (2008), 180:2581-2587.
Spees; et al., "Differentiation, cell fusion, and nuclear fusion during ex vivo repair of epithelium by human adult stem cells from bone marrow stroma", PNAS (2003), 100(5):2397-2402.
Wagers; et al., "Little Evidence for Developmental Plasticity of Adult Hematopoietic Stem Cells", Science (2002), 297:2256-2259.

*Primary Examiner* — Gary Benzion
*Assistant Examiner* — Cynthia Wilder
(74) *Attorney, Agent, or Firm* — Bozicevic, Field & Francis LLP; Pamela J. Sherwood

(57) ABSTRACT

Methods and compositions are provided for the isolation, culture and use of highly regenerative somatic mammalian cells. The cells are very small, and have an undefined nuclear structure. The cells may be isolated from fetal or adult tissues, and are found in tissue including, without limitation, fetal dermal tissue, blood, and bone marrow. The cells are characterized as expressing one or more markers selected from E-cadherin, integrin β1, CXCR4, CD90 and CD34, and may be selected on the basis of such expression patterns.

9 Claims, 23 Drawing Sheets
(22 of 23 Drawing Sheet(s) Filed in Color)

REGENERATIVE DOT CELLS

FEDERALLY-SPONSORED RESEARCH OR DEVELOPMENT

This invention was made with Government support under contracts GM041343 and GM087609 awarded by the National Institutes of Health. The Government has certain rights in this invention.

Tissue damage can be caused by traumatic injury, ischemic and fibrotic disease. As a result of such damage, scarring can happen in different tissue and organs, such as skin, liver and heart. In skin, patients with large scars have life long psychological and physical burdens, since no proven therapy for scarring exists. In cardiovascular diseases, an acute heart attack may be induced by ischemia of cardiomyocytes, which can result in the necrosis of heart tissue and leads to scar formation in heart. Therefore, finding therapy to regenerate damaged tissue or organs is of great interest in clinical medicine. While stem cells are believed to have great potential for regeneration of damaged tissues, some reports have been contradictive, for example in the use of adult bone marrow stem cells to regenerate cardiomyocytes. Further, conventional bone marrow stem cells have been reported to lose the ability to regenerate tissue after in vitro culture.

Bone marrow (BM) or blood-derived hematopoietic stem cells (HSCs) have been reported to participate in the development and regeneration of tissues outside of hematopoietic lineages. For example, unfractionated bone marrow cells have been shown to regenerate muscle, neurons, hepatocytes, smooth muscle cells and other tissues, indicating the presence of stem cells. However, a specific bone marrow or blood-derived stem cell subpopulation(s) with multi-lineage potential has not been identified.

Some research indicates that bone marrow contains at least two types of stem cells: HSCs that are c-kit$^+$ lin$^-$ sca1$^+$, which only differentiate to hematopoietic tissues; and mesenchymal stem cells (MSCs) that differentiate towards osteogenic, adipogenic, myogenic and chondrogenic lineages. Additionally, stromal cells in bone marrow have been reported to include multipotent adult progenitor cells (MAPCs), characterized as CD34$^-$ CD44$^-$ CD45$^-$ c-kit$^-$; marrow-isolated adult multi-lineage inducible (MIAMI) cells, characterized as CD29$^+$, CD63$^+$, CD81$^+$, CD122$^+$, CD164$^+$, CD34$^-$, CD36$^-$, CD45$^-$ and c-kit$^-$. Other adult stem cells populations reported to have multilineage potential include unrestricted somatic stem cells (USSCs), characterized as CD34$^{lo}$ CD45$^-$ c-kit$^{lo}$; and amniotic fluid-derived stem (AFS) cells that express similar surface markers to USSCs. Cell surface markers that have been reported to identify multilineage stem cells include integrin β1, CD34, integrin α6, P63 and keratin19, (for example see Roybon et al. (2006) Stem Cells 24:1594; and Jiang et al. (2002) Nature 418:41). However, although attempts have been made to prospectively isolate stromal stem cells with multi-lineage potential, the results are still unclear or controversial.

The mechanism of tissue regeneration by stem cells occurs through differentiation. The plasticity of stem cells may occur through either direct cellular transdifferentiation or fusion-dependent transdifferentiation. Many studies find that BM stem cell-mediated tissue regeneration occurs by stem cell direct transdifferentiation, which has been observed for hepatocytes, cardiomyocytes, neurons and skin cells. The majority of researchers claim that the direct cellular transdifferentiation of stem cells is regulated by extracellular signals. However, fusion-induced transdifferentiation of BM stem cells occurs in vitro through co-culture with other types of cells, such as epithelial cells and neurons, and occurs in vivo with hepatocytes, intestinal stem cells, cardiomyocytes, and neurons after MSC transplantation. The plasticity of stem cells has been explained by stem cell-target cell fusion, in which the stem cell acquires the features of the differentiated cell. These observations describe the importance of cell fusion during tissue regeneration. However, fusion-dependent trans-differentiation likely occurs in low frequency, suggesting a low number of fusogenic cells in the bone marrow. Thus, the biological significance of fusion-derived tissue regeneration may be low under normal physiological conditions. These observations also suggest that MSC differentiation occurs in systemic microenvironments and not in the BM.

BM stem cells have the capability to self-renew as they maintain a constant number and also supply progenitor cells for tissues. Although the self-renewal of stem cells has been suggested through an asymmetric division, however, how a single cell can divide to produce two cells that adopt different fate is totally unknown. Self-renewal of BM stem cells has only been detected in vivo after freshly isolated cell transplantation. In vitro expanded BM stem cells lost their regenerative activity, which may be due to their immediate differentiation, but brings into questions about the existence of these cultured stem cells and the choices of the markers for stem cell isolation.

Other skin-derived precursor cells have been isolated from neonatal and adult skin. These cells express nestin, fibronectin and bIII tubulin and can differentiate into both neural and mesodermal cell types (see D'Ippolito et al., (2004) *J Cell Sci* 117:2971. One group also reported that epithelial stem cells that were isolated from the fetal dermis express E-cadherin, cytokeratin-8, -18, -19, p63 and integrin β1 (Kogler et al. (2004) *J Exp Med* 200, 123). In addition, participation of bone marrow or blood-derived hematopoietic stem cells (HSCs) have been proposed in tissue development and regeneration (see, for example, Wagers et al. (1997) *Science* 297:2256; Chiavegato et al. (2007) *J Mol Cell Cardiol* 42, 746; and Holden (2007) *Science* 315, 760.

The identification and isolation of regenerative skins from post-natal tissues is of great interest for a variety of clinical and research purposes. The present invention addresses this need.

Publications

Publications relating to fusion and trans-differentiation of stem cells include Jang et al. Nat Cell Biol 6, 532 (June, 2004); Newsome et al., Gastroenterology 124, 1891 (June, 2003); Eisenberg et al. Stem Cells 24, 1236 (May, 2006); Cogle et al., Lancet 363, 1432 (May 1, 2004); Sasaki et al., J Immunol 180, 2581 (Feb. 15, 2008); Spees et al., Proc Natl Acad Sci USA 100, 2397 (Mar. 4, 2003); Alvarez-Dolado et al., Nature 425, 968 (Oct. 30, 2003); Nygren et al., Nat Med 10, 494 (May, 2004); Petersen et al., Science 284, 1168 (May 14, 1999); Rizvi et al., Proc Natl Acad Sci USA 103, 6321 (Apr. 18, 2006); Johansson et al., Nat Cell Biol 10, 575 (May, 2008); and Vassilopoulos et al. Nature 422, 901 (Apr. 24, 2003).

SUMMARY OF THE INVENTION

Methods and compositions are provided for the isolation, culture and use of mammalian Dot cells. Dot cells are highly regenerative, and find use in a variety of situations for repair of skin wounds, cardiac damage and blood vessel damage. Dot cells are very small cells, having an average size of about 0.5 µm, and having an undefined nuclear structure and generally lacking intracellular organelles. Dot cells may be isolated from fetal or adult tissues, and are found in tissue including, without limitation, fetal dermal tissue, blood, and bone marrow. The cells are characterized as expressing one or more markers selected from E-cadherin, integrin β1, CXCR4, CD90 and CD34, and may be selected on the basis of such expression patterns. Dot cells also express transcription factors characteristic of stem cells, including Oct/4, Nanog and Sox-2

In some embodiments of the invention compositions of purified Dot cells are provided. In other embodiments, methods are provided for the separation and characterization of Dot cells. Circulating Dot cells migrate to wounds and differentiate, inter alia, into dermal cells, endothelial cells and cardiomyocytes, resulting in the healing of skin and heart with reduced scarring. Both in vitro and in vivo animal studies have been performed, demonstrating the appearance of Dot cells in damaged tissue, such as wounds and infarcted heart after intravenous injection. Dot cells did not induce immune rejection after transplantation into different strains in mice.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 3A and 3B shows the cultured tiny dot shaped cells imaged by inverted microscope using phase contract light. In 3A, a fibroblast (thin arrow) was used for Dot cell size comparison. 3B shows Dot cells forming tight cell-cell connected monolayer with undistinguishable cell membrane boundary. FIG. 3C shows the E cadherin stain on cultured Dot cells. Cultured Dot cells were fixed and stained with fluorescent labeled E-cadherin (red). The staining was examined using confocal microscope. E-cadherin was stained as dots shape in Dot cells, indicating that E-cadherin is expressed not only on the cell membrane but also intracellularly. 3D shows the FACS analysis for E-cadherin expression in cultured Dot cells. More than 70% of cells were positive for E-cadherin in separate experiments after one month in culture (N≧4). Bar=100 µm in A and B; Bar=10 µm in C.

FIG. 7C shows immunoblot of SMA expression in wounds collected from adult Dot cell-transplantation mice (DC) and saline injected group (Con). Again, there is reduced SMA expression in adult Dot cell transplanted wounds from day 8 and after.

DESCRIPTION OF THE SPECIFIC EMBODIMENTS

Figure 1:
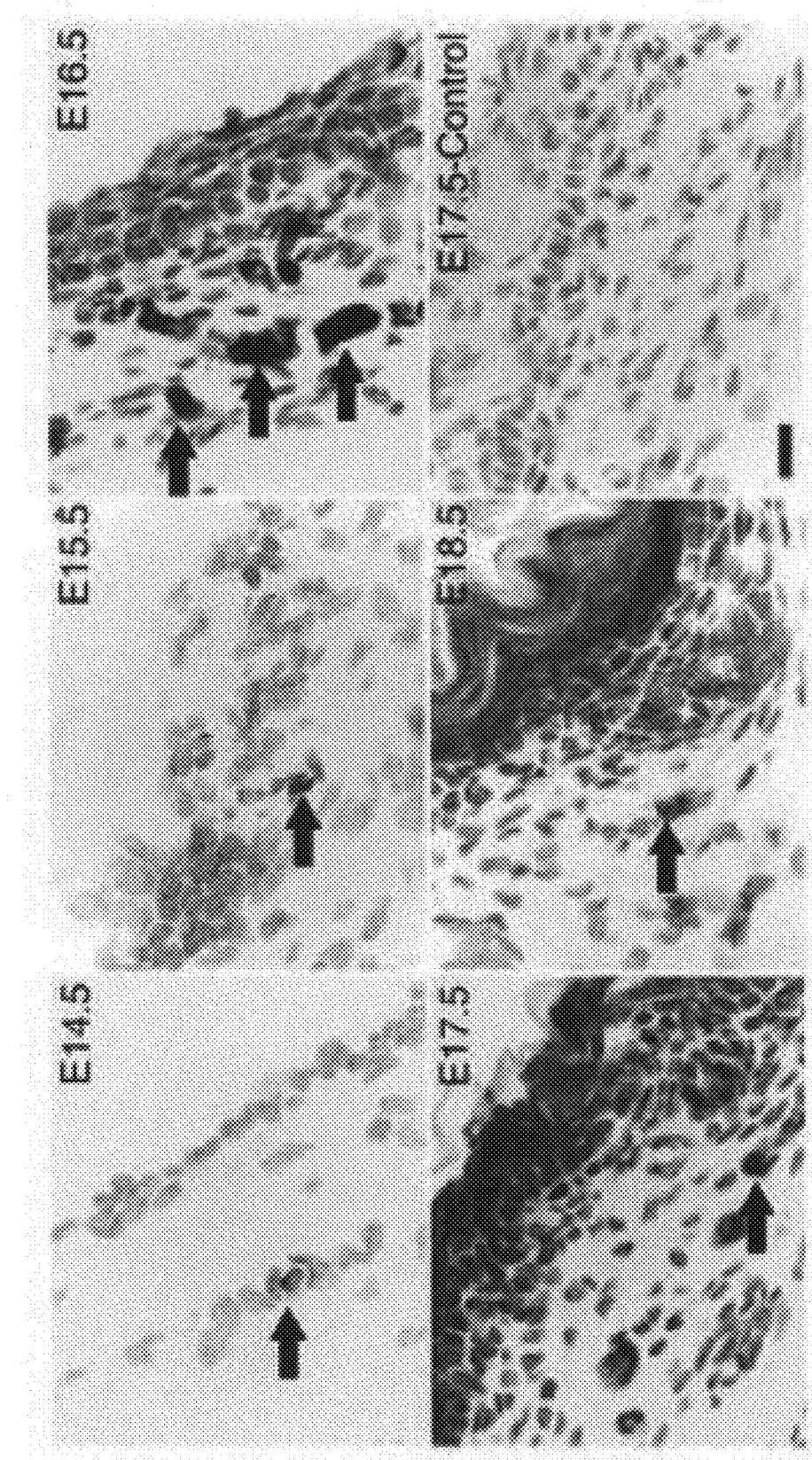
FIG. 1. Identification of Dot cells in dermis of fetal mice skin. Dorsal skin was collected from E14.5 to E18.5 fetal mice and the expression of E-cadherin was analyzed in dorsal skin of E14.5 to E18.5 fetal mice using IHC. The control section was performed without primary antibody. Arrows indicate the strongly stained E-cadherin positive cells, with the highest number of dermal E-cadherin cells on E16.5 compared to other fetal sections. By E18.5, E-cadherin was expressed mainly in epithelial cells. Bars=40 µm.

Methods are provided for the separation and characterization of mammalian Dot cells; and compositions of cells enriched for Dot cells are provided. Use of a procedure that separates Dot cells from blood or bone marrow provides a highly enriched population, which population can be used in research, transplantation, culture in vitro, etc. The ability to sort these cells facilitates their use in tissue regeneration, as well as determination of cell lineage relationships in the differentiation of stem cells, and the determination of the signaling pathways and gene expression dynamics important for these cell populations. In vitro and in vivo systems are provided for the growth and analysis, including clonal analysis, of Dot cells. Included as in vivo systems are animal models in which Dot cells, e.g. Dot cells comprising a detectable marker, are introduced. Dot cells are also grown in vitro, for maintenance or expansion.

The subject cells are useful in transplantation, for the regenerative healing of skin wounds; following traumatic damage; heart damage; and the like. These cells can also differentiate into epithelial cells, osteoblasts, cardiomyocytes, bone marrow cells and neurons. The cells are also useful for experimental evaluation, and as a source of lineage and cell specific products, including mRNA species useful in identifying genes specifically expressed in these cells, and as targets for the discovery of factors or molecules that can affect them.

The differentiation of Dot cells is regulated by the microenvironment, i.e. the type of adjacent cells. Dot cells differentiate into osteoblasts when they were co-cultured with osteoblasts, differentiate into cardiomyocytes when they were co-cultured with cardiomyocytes, differentiate into epithelial cells when they were co-cultured with epithelia cells, and differentiate into dermal cells when they were co-cultured with dermal fibroblasts. Dot cells also differentiate into endothelial cells. Dot cells have been cultured for more than 10 passages, and after freezing and thawing, Dot cells maintain their regenerative potential.

Without limiting the scope of the invention, it is believed that the mechanism of Dot cell multi-lineage differentiation is through Dot cell self-fusion. When Dot cells are grown in a co-culture environment, they aggregate first, then multiple Dot cells fuse to form a cell that resembles a normal eukaryotic cell, i.e. with a defined nuclear membrane. The cytoplasmic and nuclear components of the newly formed cell are derived by the fusion of Dot cells. After fusion, the cell membrane is formed by the connection of multiple dot cell membrane, while the nuclear of the newly formed eukaryotic cell is formed by the combination of nuclear material of multiple Dot cells, or through nuclear reprogramming of a dominant Dot cell. Dot cell fusion has been observed in both in vitro and in vivo experiments in skin and in cardiomyocytes. Dot cells are stem cells having the developmental potential to differentiate into multiple distinct lineages, e.g. skin, cardiac muscle, neurons, etc. as described herein. They are apparently more primitive than previously described somatic stem cells. Dot cells are not observed to express major histocompatibility antigens, e.g. HLA A, B, C, H2 K or D antigens, and thus have low immunogenicity.

In one aspect of the invention, Dot cells may be used to physiologically repair damaged tissue(s) of the skin without scars, such as the skin of a deep second degree burn (or partial thickness burn) that has destroyed the epidermis, the basal layer, and severely damaged the dermis. The methodology may also be used to regenerate skin with restoration of structures and functions of the epidermis, dermis and various appendages of the skin. For example, a patient with both epidermis and dermis destroyed by fire or chemical, i.e., superficial third degree burn or full thickness burn, can be treated with the methodology without substantial loss of physiological functions of the skin, including those of the appendages.

The Dot cells are useful in transplantation, including the regeneration of skin, e.g. in the treatment of burns, surgery; following traumatic damage, for cosmetic purposes, in the treatment of keloids and fibrosis; and the like. For such purposes the cells may be introduced systemically, e.g. by iv injection, or locally. In skin wounds, more Dot cells were detected during the time of wound repair. Following repair, few Dot cells were seen in the area of tissue damage.

In addition, the methodology of the present invention may also be used for regenerating skin that has been damaged by other types of wounds including but not limited to trauma, surgical and infected wounds; surface ulcers including but not limited to chronic ulcers, diabetic ulcers, decubital ulcer, and lower limb vascular disease, and other non-healing wounds as result of poor blood flow; wounds and/or erosions caused by bacterial and viral infection, such as vaginitis, cervical erosion, gingivitis; wounds due to dilation and enlargement of veins such as hemorrhoids; herpes simplex corneal ulcer, subcutaneous tissue ulcer, radiation-caused skin ulcer, wounds caused by wind and cold such as chilblain and chapped skin. By using the compositions provided by the present invention, these types of wounds can be treated and heal physiologically without disfigurement and disablement.

In another aspect of the invention, Dot cells may be used to physiologically repair damaged tissue(s) of the heart damage, for example from acute or chronic heart disease.

The cells also find use of cardiovascular repair, for example in the acute stage following myocardial infarction or other conditions associate with damage to cardiac muscle tissue. Dot cells migrate into damaged area to differentiate into newly formed cardiomyocytes. Transplanted Dot cells migrate to heart ischemic area and constantly repair the damage until it is fully recovered. It was found that numerous Dot cells were located near heart ischemic areas even 4 weeks after iv injection, indicating that the regenerative function of Dot cells can last as long as the tissue or organ needs to be repaired.

In another aspect of the invention Dot cells are used to physiologically repair damaged tissue(s) of the bone marrow, e.g. as a result of disease, chemotherapy, etc.

Dot cells may be isolated from peripheral blood, and are found in tissue including, without limitation, fetal dermal tissue, blood, and bone marrow. Cellular compositions may be freshly isolated, frozen, maintained or expanded in culture, etc. Dot cell compositions may be freshly isolated, frozen, maintained or expanded in culture, etc. Populations of Dot cells may be obtained by selection of cells from a complex mixture, e.g. a patient or donor sample, on the basis of expression of specific cell surface markers to provide a substantially pure population of Dot cells. The cells are characterized as rapidly proliferating cells of from about 0.1 to about 2 μm in diameter. Usually the cells are suspended in a physiologically acceptable medium.

Dot cells that are freshly isolated from blood express E-cadherin and integrin β1, CD184, CD34, CD90, $CD13^{low}$ and $Sca1^{low}$, but are negative for expression of CD45, CD44, and CD117. However, after one month or longer time culture, the expression of the surface markers changed, E-cadherin, integrin β1 and CD184/CXCR4 decreases while the expression of CD117 and CD45 increases. The expression of CD90 and CD34 do not change in culture.

As used herein, a "substantially pure population" means that the population has less than about 20%, preferably less than about 10%, more preferably less than about 8%, even more preferably less than about 5%, and yet even more preferably less than about 1%, e.g., less than a detectable amount as determined by methods known to the art, of cells which are not Dot cells.

Cells for transplantation are usually autologous or allogeneic with respect to the recipient, and when allogeneic may be matched to the recipient for one or more MHC antigens. Dot cells have not been found to express MHC/HLA antigens and are therefore well-suited for transplantation across class I MHC differences. It has been found that transplantation of Dot cells between different mouse stains did not induce graft rejection. For example, GFP-transgenic mouse (FVB.Cg-Tg (ACTB-EGFP)B5Nagy/J)—isolated Dot cells were transplanted to Balb/c mouse; and Balb/c mouse-isolated Dot cells were transplanted to diabetic mouse (B6.Cg-m+/+Leprdb/J). Transplanted Dot cells regenerated to skin across MHC differences.

DEFINITIONS

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "an", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Dot cells As used herein, the term Dot cells refers to small cells having an undefined nucleus, found in mammals, including humans, mice and rats. Dot cells contribute to tissue regeneration of lineages derived from ectoderm, endoderm and mesoderm. The cells can be involved in skin, bone, cardiomyocytes, epithelial regeneration and act in the organization of remodeling of skin tissue, without generating long-lived progenitor cells in situ. The phenotype of the cells is as described in detail herein.

For many purposes, the primary requirement of a progenitor cell is an ability to contribute to tissue formation in vivo, e.g. in injured skin, injured cardiac tissue, etc. Preferred progenitors contribute to regeneration in a manner that results in decreased scarring when compared to comparable formation in the absence of exogenously provided progenitor cells. It should be understood that exogenous cells may be of allogeneic or autologous origin, but will be administered to a recipient systemically or locally to enhance tissue regeneration. As shown herein, E-cadherin Dot cells have this capability.

Under appropriate conditions in vitro, the Dot cells will form a monolayer of cells that maintain expression of E-cadherin, β1-integrin, CXCR4, CD90 and CD34, for extended periods of time, e.g. for at least about 2 week, 4 weeks or longer. When Dot cells reach confluence, they also form spheroids, as described with embryonic stem cells. Dot cells can be passaged indefinitely and frozen in liquid nitrogen and thawed to grow back in culture. Conditions for culture may include the presence of a substrate, such as collagen or laminin; and will include conventional medium and excipients, as is known in the art.

The in vivo stem/progenitor capability of Dot cells is evidenced by the ability to regenerate skin at wound sites, and cardiomyocytes at ischemia induced heart damage, following administration to the recipient. Administration may be systemic, e.g. i.v. administration; may be intradermal, e.g. by injection at the site of the wound, or topical, e.g. at the site of the tissue damage.

Skin is the largest organ of an animal, consisting of outer epidermis, dermis, and hypodermis. Normal, physiologically functional skin has these three layer of tissues interact with each other in structurally distinctive patterns. The epidermis is a continually renewing, stratified, squamous epithelium. Most of the cells in the epidermis are keratinocytes arranged in layers that represent different stages of their differentiation. The outer layer, the horny layer, functions as a barrier. It protects the body from the environment and helps maintain the internal milieu. The dermis, the connective tissue matrix of the skin, gives the skin its structural strength, protects the body from injury, stores water, and interacts with the epidermis. The papillae of the dermis mirror the contours of the epidermis, i.e., the alternating ridges and valleys of the underside of the epidermis.

The histologic hallmark of scarless fetal wound healing is the regeneration of dermal appendages and surrounding muscles. Cutaneous scarring may be defined as macroscopic disturbance of normal architecture, resulting from the end product of a healed wound, and may manifest itself as an elevated or depressed site with an alteration of skin texture, color, vascularity, nerve supply, reflectance, and biochemical properties. Ferguson et al. (1996) Plast. Reconstr. Surg. 97:854. Histologically, scarring may be defined as the microscopic alteration of tissue architecture, with collagen deposition and organization that differ from the surrounding unwounded tissues.

Involvement of the Dot cells at the site of a wound can result in the regeneration of skin with reduced scarring in the patient. Skin regeneration as used herein refers to the process by which new skin layers form from skin progenitor cells, e.g. in a wound context. A therapeutic composition will usually result in the generation of skin with reduced scarring. The production of scar tissue at the site of regeneration can be monitored visually, histologically, proteomically, etc., where the tissue may be examined for gross changes in the degree of cellular infiltration, granulation tissue formation, vascularity, re-epithelialization, collagen deposition, etc. A wound with reduced scarring will usually have at least about a 10% decrease in one or more indicia of scarring, at least about a 20% decrease, at least about a 30% decrease, at least about a 50% decrease, at least about a 75% decrease, or more. The growth of skin may be measured by an increase in wet weight, an increase in protein content, an increase in skin thickness; etc.

E-cadherin is a transmembrane protein that is expressed on epithelial cells, mast cells, brain endothelial cells, and skin Langerhans cells. Cadherins are a class of type-1 transmembrane proteins. They play important roles in cell adhesion, ensuring that cells within tissues are bound together. They are dependent on calcium ions to function, hence their name.

The cadherin superfamily includes cadherins, protocadherins, desmogleins, and desmocollins, and more. In structure, they share cadherin repeats, which are the extracellular Ca2+-binding domains. Cadherins within one class will bind only to themselves. Because of this specificity, groups of cells that express the same type of cadherin molecule tend to cluster together during development, whereas cells expressing different types of cadherin molecules tend to separate.

E-cadherin consists of 5 cadherin repeats (EC1~EC5) in the extracellular domain, one transmembrane domain, and an intracellular domain that binds p120-catenin and beta-catenin. The intracellular domain contains a highly-phosphorylated region vital to beta-catenin binding and therefore to E-cadherin function. Beta-catenin can also bind to alpha-catenin. Alpha-catenin participates in regulation of actin-containing cytoskeletal filaments. In epithelial cells, E-cadherin-containing cell-to-cell junctions are often adjacent to actin-containing filaments of the cytoskeleton.

Positive and negative staining. The subject Dot cells are characterized by their expression of cell surface markers. While it is commonplace in the art to refer to cells as "positive" or "negative" for a particular marker, actual expression levels are a quantitative trait. The number of molecules on the cell surface can vary by several logs, yet still be characterized as "positive". It is also understood by those of skill in the art that a cell which is negative for staining, i.e. the level of binding of a marker specific reagent is not detectably different from a control, e.g. an isotype matched control; may express minor amounts of the marker. Characterization of the level of staining permits subtle distinctions between cell populations.

The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but it is not as intense as the most brightly staining cells normally found in the population. Low positive cells may have unique properties that differ from the negative and brightly stained positive cells of the sample. An alternative control may utilize a substrate having a defined density of marker on its surface, for example a fabricated bead or cell line, which provides the positive control for intensity.

Sources of Progenitor Cells. Ex vivo and in vitro cell populations useful as a source of cells may include fresh or frozen cell populations obtained from embryonic, fetal, pediatric or adult tissue. Tissues in which Dot cells are found include blood, bone marrow and other circulatory compartments, as well as dermal tissue and surrounding muscle and connective tissues. The methods of selection can include further enrichment or purification procedures or steps for cell isolation by selection for cell specific markers, cell size, etc. The Dot cells may be obtained from any mammalian species, e.g. human, equine, bovine, porcine, canine, feline, rodent, e.g. mice, rats, hamster, primate, etc.

Markers. The markers for selection of epidermal progenitors and/or BM derived epidermal cells will vary with the specific cells. As described above, a number of well-known markers can be used for positive selection and negative selection. Dot cells are particularly small cells, and can sorted on that basis, e.g. by forward scatter, etc. Useful markers for positive selection may include, without limitation, E-cadherin. Additional or alternative markers for positive selection include integrin β1, CD184, CD34, $CD13^{low}$ and $Sca1^{low}$. Markers for negative selection include, without limitation, CD45, CD44, and CD117.

Specific Binding Member. The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). The complementary members of a specific binding pair are sometimes referred to as a ligand and receptor; or receptor and counter-receptor. Such specific binding members are useful in positive and negative selection methods. Specific binding pairs of interest include carbohydrates and lectins; complementary nucleotide sequences; peptide ligands and receptor; effector and receptor molecules; hormones and hormone binding protein; enzyme cofactors and enzymes; enzyme inhibitors and enzymes; antibodies and antigens; etc. The specific binding pairs may include analogs, derivatives and fragments of the original specific binding member. For example, a receptor and ligand pair may include peptide fragments, chemically synthesized peptidomimetics, labeled protein, derivatized protein, etc.

Especially useful reagents are antibodies specific for markers present on the desired cells (for positive selection) and undesired cells (for negative selection). Whole antibodies may be used, or fragments, e.g. Fab, $F(ab')_2$, light or heavy chain fragments, etc. Such selection antibodies may be polyclonal or monoclonal and are generally commercially available or alternatively, readily produced by techniques known to those skilled in the art. Antibodies selected for use will have a low level of non-specific staining and will usually have an affinity of at least about 100 µM for the antigen.

In one embodiment of the invention, antibodies for selection are coupled to a label. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red, cy7, cy5. Frequently each antibody is labeled with a different fluorochrome, to permit independent sorting for each marker. The exact method for coupling to a label is not critical to the practice of the invention, and a number of alternatives are known in the art. Direct coupling attaches the antibodies to the label. Indirect coupling can be accomplished by several methods. The antibodies may be coupled to one member of a high affinity binding system, e.g. biotin, and the particles attached to the other member, e.g. avidin. One may also use second stage antibodies that recognize species-specific epitopes of the antibodies, e.g. anti-mouse Ig, anti-rat Ig, etc. Indirect coupling methods allow the use of a single labeled entity, e.g. antibody, avidin, etc., with a variety of separation antibodies.

Enrichment Methods

The subject Dot cells are separated from a complex mixture of cells by techniques that enrich for cells having the characteristics as described. For example, a blood sample may be obtained from a donor or a pool of donors. From this population, cells may be selected for expression of E-cadherin. The cells are optionally selected for one or more of the positive or negative markers recited herein. In addition the cells may be selected for a size ranging from around about 0.1 µM in diameter to less than about 2 µM in diameter, usually less than about 1 µM in diameter and may be, on average around about 0.5 µm in diameter.

Where the sample is blood cells, no dissociation is required, although removal of red blood cells may be convenient. Solid tissues may be dissociated by digestion with a suitable protease, e.g. collagenase, dispase, etc., followed by trituration until dissociated. An appropriate solution is used for dispersion or suspension. Such solution will generally be a balanced salt solution, e.g. normal saline, PBS, Hanks balanced salt solution, etc., supplemented with fetal calf serum or other naturally occurring factors, in conjunction with an acceptable buffer at low concentration, generally from 5-25 mM. Convenient buffers include HEPES, phosphate buffers, lactate buffers, etc.

Separation of the subject cell population will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, 7-AAD). Any technique may be employed which is not unduly detrimental to the viability of the selected cells.

The affinity reagents may be specific receptors or ligands for the cell surface molecules indicated above. The details of the preparation of antibodies and their suitability for use as specific binding members are well known to those skilled in the art. Of particular interest is the use of antibodies as affinity reagents.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells: A preferred medium is phosphate buffered saline containing from 0.1 to 0.5% BSA. Various media are commercially available and may be used according to the nature of the cells, including Dulbeccos Modified Eagle Medium (dMEM), Hank's Basic Salt Solution (HBSS), Dulbeccos phosphate buffered saline (dPBS), RPMI, Iscoves medium, PBS with 5 mM EDTA, etc., frequently supplemented with fetal calf serum, BSA, HSA, etc.

The labeled cells are then separated as to the phenotype described above. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscoves medium, etc., frequently supplemented with fetal calf serum.

Compositions highly enriched for Dot cells are achieved in this manner. The subject population will be at or about 50% or more Dot cells, and usually at or about 90% or more of the cell composition, and may be as much as about 95% or more of the live cell population. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded in culture for proliferation and differentiation.

The compositions thus obtained have a variety of uses in clinical therapy, research, development, and commercial purposes. For therapeutic purposes, for example, Dot cells may be administered to enhance tissue maintenance or repair of muscle for any perceived need, such as an inborn error in metabolic function, the effect of a disease condition, or the result of significant trauma.

To determine the suitability of cell compositions for therapeutic administration, the cells can first be tested in a suitable animal model. At one level, cells are assessed for their ability to survive and generate the desired phenotype in vivo. Cell compositions may be administered to immunodeficient animals (such as nude mice, or animals rendered immunodeficient chemically or by irradiation). Tissues are harvested after a period of regrowth, and assessed as to whether the administered cells or progeny thereof are still present.

This can be performed by administering cells that express a detectable label (such as green fluorescent protein, or β-galactosidase); that have been prelabeled (for example, with BrdU or [$^3$H] thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

Suitability can also be determined in an animal model by assessing the degree of skin regeneration that ensues from treatment with the cells of the invention. A number of animal models are available for such testing. For example, skin can be wounded as described in the Examples. Injured sites are treated with cell preparations of this invention systemically or locally, and the skin tissue is examined by histology for the presence of the cells in the damaged area, and for the regeneration of skin tissue.

Cells may be genetically altered in order to introduce genes useful in the differentiated cell, e.g. repair of a genetic defect in an individual, selectable marker, etc. Cells may be genetically altering by transfection or transduction with a suitable vector, homologous recombination, or other appropriate technique, so that they express a gene of interest. In some embodiments, a selectable marker is introduced, to provide for greater purity of the desired cell. Cells may be genetically altered using vector containing supernatants over an 8-16 h period, and then exchanged into growth medium for 1-2 days. Genetically altered cells are selected using a drug selection agent such as puromycin, G418, or blasticidin, and then recultured. Genetically modified cells can also be selected for a detectable marker, e.g. GFP, etc., by cell sorting methods known in the art.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. Retrovirus based vectors have been shown to be particularly useful when the target cells are progenitor cells. For example, see Schwarzenberger et al. (1996) Blood 87:472-478; Nolta et al. (1996) P.N.A.S. 93:2414-2419; and Maze et al. (1996) P.N.A.S. 93:206-210.

Combinations of retroviruses and an appropriate packaging line may be used, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

Lentiviral vectors such as those based on HIV or FIV gag sequences can be used to transfect non-dividing cells, such as the resting phase of human stem cells (see Uchida et al., (1998) P.N.A.S. 95(20):11939-44).

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) *Mol. Cell. Biol.* 5:431-437); PA317 (Miller et al. (1986) *Mol. Cell. Biol.* 6:2895-2902) GRIP (Danos et al., (1988) *PNAS* 85:6460-6464). Retroviruses packaged with xenotropic envelope protein, e.g. AKR env, are capable of infecting most mammalian cell types, except murine cells.

The vectors may include genes that must later be removed, e.g. using a recombinase system such as Cre/Lox, or the cells that express them destroyed, e.g. by including genes that allow selective toxicity such as herpesvirus TK, bcl-xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

Therapeutic Methods

The Dot cells may be used for tissue reconstitution or regeneration in a human patient or other subject in need of such treatment. The cells are administered in a manner that permits them to graft or migrate to the intended tissue site and reconstitute or regenerate the functionally deficient area.

The differentiating cells may be administered in any physiologically acceptable excipient, where the cells may find an appropriate site for regeneration and differentiation. The cells may be introduced by injection, catheter, or the like. The cells may be frozen at liquid nitrogen temperatures and stored for long periods of time, being capable of use on thawing. If frozen, the cells may be stored in conventional freezing medium, e.g. a 10% DMSO, 50% FCS, 40% RPMI 1640 medium. Once thawed, the cells may be expanded in culture, optionally including use of growth factors and/or feeder cells associated with progenitor cell proliferation and differentiation.

The cells of this invention can be supplied in the form of a pharmaceutical composition, comprising an isotonic excipient prepared under sufficiently sterile conditions for human administration. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease. The therapeutic effect can be measured in terms of clinical outcome or can be determined by immunological or biochemical tests.

The dosage of the therapeutic formulation will vary widely, depending upon the nature of the condition, the frequency of administration, the manner of administration, the clearance of the agent from the host, and the like. The initial dose is usually provided shortly after injury, or in anticipation of injury, e.g. during surgery. For systemic administration, the effective dose may be from around about $10^3$ cells/kg body weight;

from around about $10^4$ cells/kg body weight; from around about $10^5$ cells/kg body weight; to around about $10^5$ cells/kg body weight; or more. Where administration is localized, e.g. by intradermal or topical administration, the dose may be reduced.

Libraries

The cells of this invention can be used to prepare a cDNA library relatively uncontaminated with cDNA preferentially expressed in cells from other lineages. For example, dermal progenitors are collected by centrifugation at 1000 rpm for 5 min, and then mRNA is prepared from the pellet by standard techniques (Sambrook et al., supra). After reverse transcribing into cDNA, the preparation can be subtracted with cDNA from other progenitor cells, or end-stage cells from the dermal or any other developmental pathway.

The cells of this invention can also be used to prepare antibodies that are specific for markers of dermal cells and their precursors. Polyclonal antibodies can be prepared by injecting a vertebrate animal with cells of this invention in an immunogenic form. Production of monoclonal antibodies is described in standard references. Specific antibody molecules can also be produced by contacting a library of immunocompetent cells or viral particles with the target antigen, and growing out positively selected clones. See Marks et al., New Eng. J. Med. 335:730, 1996, and McGuiness et al., Nature Biotechnol. 14:1449, 1996. A further alternative is reassembly of random DNA fragments into antibody encoding regions, as described in EP patent application 1,094,108 A.

The antibodies in turn can be used to identify or rescue cells of a desired phenotype from a mixed cell population, for purposes such as costaining during immunodiagnosis using tissue samples, and isolating precursor cells from dermal tissue and cells of other lineages.

Of particular interest is the examination of gene expression in the cells of the invention. The expressed set of genes may be compared against other subsets of cells, against other stem or progenitor cells, against adult muscle tissue, and the like, as known in the art. Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+ mRNA. One of skill in the art can readily use these methods to determine differences in the size or amount of mRNA transcripts between two samples.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., Science (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. No. 5,776,683; and U.S. Pat. No. 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. No. 5,134,854, and U.S. Pat. No. 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with an array are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., Genome Res. (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

In another screening method, the test sample is assayed for the level of polypeptide of interest. Diagnosis can be accomplished using any of a number of methods to determine the absence or presence or altered amounts of a differentially expressed polypeptide in the test sample. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.) The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

Screening Assays

The cells are also useful for in vitro assays and screening to detect factors that are active on skin regenerating cells. Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, viruses, etc. the subject cells, usually a culture comprising the subject cells, is contacted with the agent of interest, and the effect of the agent assessed by monitoring output parameters, such as expression of markers, cell viability, and the like. The cells may be freshly isolated, cultured, genetically altered as described above, or the like. The cells may be environmentally induced variants of clonal cultures: e.g. split into independent cultures and grown under distinct conditions, for example with or without virus; in the presence or absence of other cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents, such as viruses, candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like.

Samples of interest include compounds being assessed for potential therapeutic value, i.e. drug candidates.

The term "samples" also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51(3):313-24, for examples.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Such biologically active products can be used in many different applications that require the regeneration of dermal tissues, including the repair of injured skin and difficult-to-heal wounds, such as burn wounds, venous stasis ulcers, diabetic ulcers, etc.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Example 1

Wounds in fetal skin heal without scar, however the mechanism is unknown. We have identified a novel group of E-cadherin positive cells in the blood of fetal and adult mice and named them "Dot cells". The percentage of Dot cells in E16.5 fetal mice blood is more than twenty times higher compared to adult blood. Dot cells also express integrin β1, CD184, CD34, CD13low and Sca1 low, but not CD45, CD44, and CD117. Dot cells have a tiny dot shape between one to seven µm diameters with fast proliferation in vitro. Most of Dot cells remain positive for E-cadherin and integrin β1 after one month in culture. Transplantation of Dot cells to adult mice heals skin wounds with less scar due to reduced smooth muscle actin and collagen expression in the repair tissue. Tracking GFP-positive Dot cells demonstrates that Dot cells migrate to wounds and differentiate into dermal cells, which also express strongly to FGF-2, and later lose their GFP expression. Our results indicate that Dot cells are a group of unidentified cells that have strong wound healing effect. The mechanism of scarless wound healing in fetal skin is due to the presence of large number of Dot cells.

Here we provide evidence that a group of blood-derived E-cadherin positive cells, Dot cells, are found in fetal dermal blood with their highest numbers on E16.5, when scarless wound healing occurs. We also identified Dot cells from the blood of human and mice, although with much lower ratio of total blood cells compared to that in fetal mice. Dot cells migrate to wounds and repair the damaged tissues through cellular differentiation. Transplantation of isolated Dot cells to wounded adult mice induces scarless healing, suggesting Dot cells are the fetal cells that responsible for scarless repair. Our data are the first to describe the Dot cells and their function during tissue repair.

Material and Methods

Animals and materials. Time dated sixteen-day (E16.5) pregnant Balb/C mice and GFP (FVB.Cg-Tg(ACTB-EGFP) B5Nagy/J, Jackson Lab) mice were bred and maintained in the Stanford Animal Care Laboratory. Mice received food and water ad libitum. All procedures with animals were conducted in accordance with university-approved protocols according to NIH guidelines. E-cadherin, integrin β1, PECAM-1, and c-kit antibodies were from Santa Cruz biotechnology (Santa Cruz, Calif.). CD34 antibody was from Abcam. CD45, Sca-1 and c-kit antibodies were from BD Pharmingen (San Diego, Calif.). Alexa Fluor goat anti-rabbit IgG was from Molecular Probes (Eugene, Oreg.). Rhodamine-labeled y-chromosome and FITC-labeled x-chromosome probes were from ID Labs (Ontario, Canada). Anti-rabbit IgG-conjugated magnetic beads and columns were from Miltenyi Biotech Inc. (Auburn, Calif.). Other chemicals were from Sigma Chemical Co., (St. Louis, Mich.).

Cell isolation using magnetic bead sorting. E16.5 timedated fetuses of Balb/C or GFP mice were collected. After removing the head, limbs and intestinal organs, whole E16.5 fetuses were minced with scissors and the mixture was then washed with PBS, centrifuged for 5 min at 35×g to remove large tissues, and filtered through 70 µm cell strainers. In pilot testing, flow cytometry-sorted cells were used. However, for all reported data, cells isolated by magnetic bead sorting were used. Magnetic bead cell sorting was followed per manufacturer's instructions. Briefly, isolated cells were blocked with blocking buffer, then reacted with anti-E-cadherin antibody for 30 min and then incubated in separation buffer for 30 min before incubation with anti-rabbit IgG conjugated magnetic beads for 30 min at 4° C. After labeling, cells in the 0.5 ml separation buffer were passed through a magnetic field MACS separation MS column followed by 3 washes with 1×PBS before elution. About 0.4% of total cells was positive and consistently obtained each time. Postnatal Dot cells were obtained by blood collection from 4-week old mice through cardiac puncture and followed by cell sorting as described above. The sorting efficiency was further confirmed by fluorescent activated cell sorting (FACS), and more than 85% cells were E-cadherin positive.

Fluorescent cell sorting (FACS). Dot cells from either freshly sorted or collected from culture conditions were washed with PBS and blocked with 1% normal horse serum (NHS) for one hour. Then, cells were labeled with different antibodies in the dilution from 1:50 or 1:100 in 100 µl PBS with 1% NHS for 30 min and followed with washes in PBS with 1% NHS and reacted with secondary antibody conjugated with either FITC (fluorescien isothiocyanate) or PE for 30 min on ice. After washing, the ratio of positive labeling was analyzed using the Vantage SE or DiVa Vantoo FACS machines at the Stanford Shared FACS Facility. Flow cytometry data was then acquired with CellQuest software (BD Biosciences) and analyzed with FlowJo software (FlowJo, Palo Alto, Calif.). Isotype antibody labeled cells was used for non-specific labeling control.

Wound creation and cell transplantation. Eight to ten week-old female Balb/C mice were anesthetized. After shaving the hair, dorsal skin was cleaned before two 0.6 cm diameter excisional wounds were made with a biopsy punch. Five hundred thousand sorted Dot cells in 100 µl normal saline were then injected with 26-gauge needle through tail-vein in each wounded mouse. The control groups were composed of tail-vein saline injection, same number of fetal fibroblasts or same number of E-cadherin positive cells sorted from postnatal mice skin.

Immunohistochemistry and immunofluorescent staining. Fetuses aged from E13.5 to E18.5 were removed from the uteri and immediately fixed in 4% paraformadehyde. All tissues were embedded in paraffin. Seven µm thickness paraffin sections were de-waxed and re-hydrated, washed three times with PBS, and treated with proteinase-k. Wounds collected from GFP-cell transplantation animals were embedded in OCT for frozen section. After washing, sections were blocked and reacted with anti-E-cadherin (1:100 dilution) overnight at 4° C. and followed by VECTASTAIN ABC kit, per instructions, and then counterstained with hematoxylin and mounted. Staining was visualized and pictured by an Axioplan 2 microscope (Zeiss). For fluorescent studies, sections were fixed, washed, blocked and then reacted with the different antibodies at dilutions ranging between 1:50 and 1:200 in blocking buffer over night at 4° C. After washing, sections were counterstained with DAPI and photographed by confocal microscopy (Leica DM IRE2) or standard fluorescent microscopy (Axioplan 2 microscope, Zeiss). The control group was treated without primary antibody. The scanned confocal images were further analyzed with Velocity software for 3 dimensional and 360-degree rotation movie images.

Protein preparation and immunoblot. Normal or wounded skin tissues were collected and stored immediately in liquid nitrogen until protein analysis. Tissues were homogenized in lysis buffer. Total protein was purified by centrifugation of tissue lysates at 12,000 g for 30 minutes at 4° C. After protein concentration was determined, thirty µg of protein from each tissue was heated at 100° C. for 5 minutes with loading buffer, then separated by 10% SDS-polyacrylamide gel and blotted onto a PVDF membrane. After reaction with anti-SMA antibody at 4° C. over night, membranes were washed and reacted with HRP-conjugated secondary antibodies. After washing, bands were visualized by blot exposure to X-ray film after 5 min reaction with ECL Western blotting detection reagents.

Electron microscopy. Dot cells were fixed with 2% glutaraldehyde and 4% paraformadehyde in sodium cacodylate buffer, pH 7.3 for 30 min at room temperature. After wash with in sodium cacodylate buffer, ice cold, 1% osmium tetroxide in distilled water was added to the cell pellet, followed with shaking gently at 4° C. for 2 hours. After washing with water, 1% uranyl acetate was added to the cell pellet for overnight. Cells were then dehydrated with serial ethanol and embedded in Epon at 65° C. for 24 hours. Ultra-thin sections were cut and doubly stained with uranyl acetate and lead citrate followed with examination using an electron microscopy.

Results

Identification of Dot cells in fetal mouse skin. We found a group of small cells that heavily express E-cadherin and are located in the dermis of fetal mice. FIG. 1 shows small cells that express E-cadherin in the dorsal skin of embryonic day E14.5 to E18.5 mice. On E14.5 and E15.5, only a few scattered small cells stained densely for Ecadherin in the dermal area (arrows). On E16.5, these small cells grouped together in clustered patterns (arrows) without clear cell-cell boundaries with dense E-cadherin staining in the dermis. Meanwhile, epithelial cells also expressed E-cadherin, but relatively weak. By E18.5, only few E-cadherin positive cells were detected in the dermal area, but epithelial cells were now strongly expressing E-cadherin.

Figure 2:
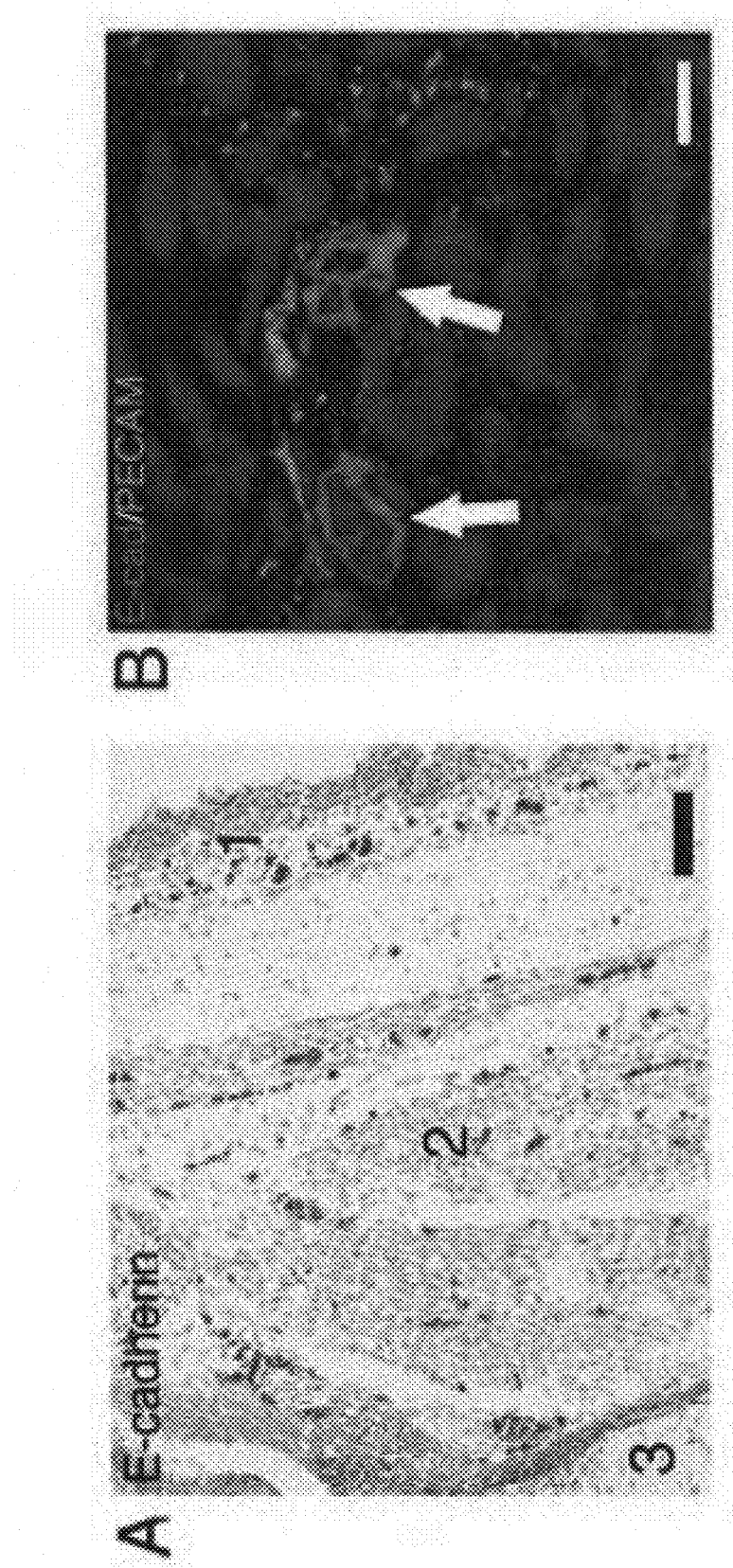
FIG. 2. Dermal E-cadherin positive cells are blood-derived. 2A shows the E-cadherin staining on section of an E16.5 fetal mouse. The epidermis had weak staining for E-cadherin, however, strongly stained and clustered E-cadherin positive cells were scattered in dermis (1), muscle (2) and areas adjacent to cartilage (3). 2B shows the immunofluorescent staining for E-cadherin and PECAM-1 examined by confocal microscope. The merged image shows that the clustered small E-cadherin positive (red) cells (arrows) in the dermis were located next to PECAM-1 (green) positive cells. Bar=300 µm in A; Bar=25 µm in B.

Dot cells are located in blood. Using a whole E16.5 fetal section (FIG. 2A), we found that clustered cells which strongly express E-cadherin were located in the dermal area (1), muscle areas (2) and adjacent to cartilage (3). To further identify the location of the dermal E-cadherin positive cells, immunofluorescent labeling for both E-cadherin and PECAM-1, a marker for endothelial cells, was examined using confocal microscopy. FIG. 2B shows the merged images of immunofluorescent staining for E-cadherin and PECAM-1 in dermis of E16.5 skin section. E-cadherin positive cells (red, arrows) were present in a clustered pattern with small nuclei located adjacent to PECAM labeled blood vessel cells (green). The nucleus size of E-cadherin positive cells was significantly smaller compared to other unstained cells.

Figure 3:
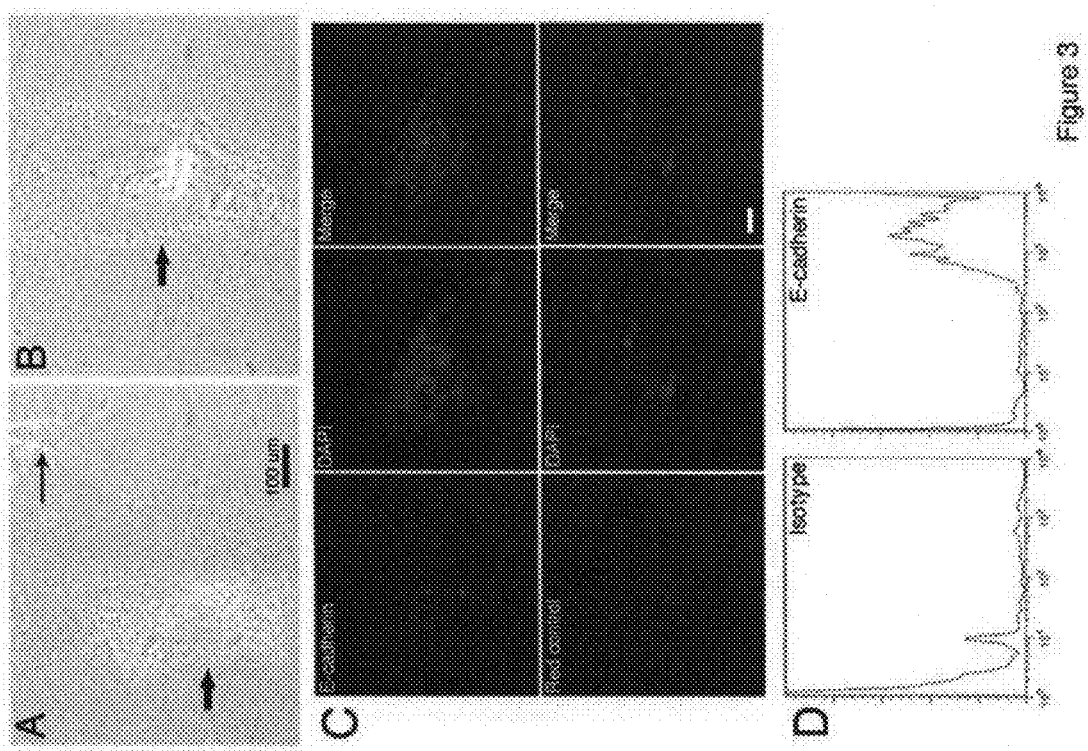
FIG. 3. In vitro culture and characterization of Dot cells. Dot cells were sorted with anti-E-cadherin antibody with magnetic beads from blood of E16.5 fetal mice and 4-week old mice, and cultured on collagen-coated plates in α-MEM with 20% FBS and antibiotics.

Blood derived E-cadherin positive cells have a "Dot" shape. Subsequently, these previously unidentified, blood-derived E-cadherin positive cells were cultured in nonfeeder-layer conditions. FIG. 3A shows that Dot cells were in tiny dots shape in culture. Their sizes ranged between two to seven µm in vitro. Dot cells formed tight cell-cell connections inside colonies. After one month in culture, more than seventy percent of cultured Dot cells were still expressing E-cadherin. FIG. 3B shows E-cadherin staining of confocal merged images of cultured Dot cells. FACS analysis for E-cadherin on cultured cells also confirmed that more than seventy percent cells were still positive for E-cadherin after one month in culture (FIG. 3C).

Figure 4:
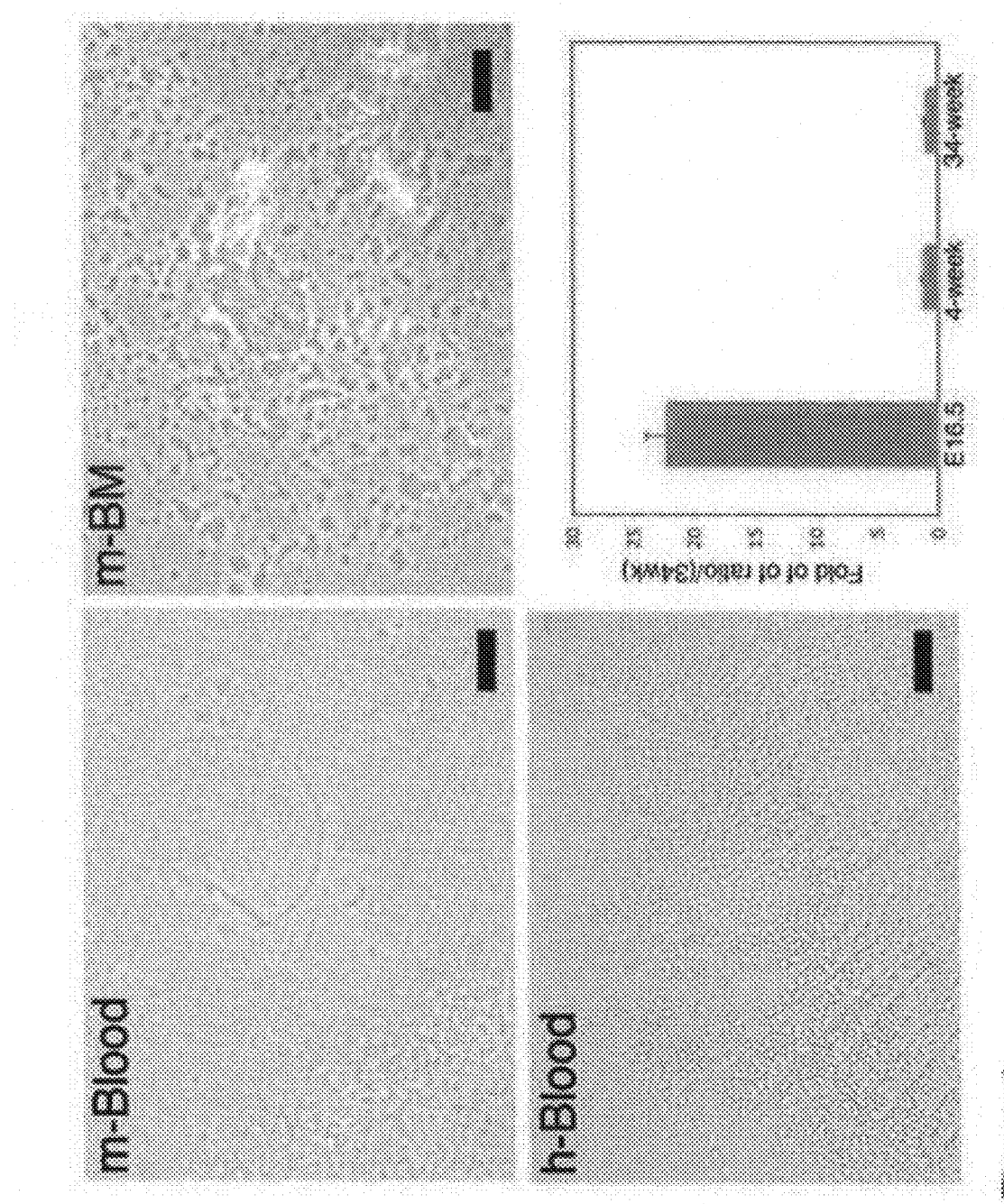
FIG. 4. Dot cells exist in blood and bone marrow of adult mice as well as in humans. Blood of adult mice was collected through cardiac puncture. Bone marrow of adult mice was also collected through long bone perfusion followed with centrifugation. In addition, blood was collected from a 48-year old man. Dot cells were cultured and images were taken using an inverted microscope. Dot cells were present in blood of mice (m-blood), bone marrow of mice (m-BM) and human blood (h-blood). The chart in FIG. 4 is the comparison of the ratio of Dot cells in blood of E16.5 fetal mice, 4-week old and 34-week old mice. There is a more than twenty times higher blood ratio of Dot cells in E16.5 fetal mice compared to that of 34-week old mice (ratio was calculated as 1).

Dot cells are present in blood of both postnatal mice and humans. To further confirm the presence of Dot cells in blood, we collected blood through cardiovascular puncture and bone marrow from 4-week old adult mice. E-cadherin sorted cells were cultured, and Dot cells were identified with inverted microscopy. In addition, human blood was collected from a 48 year-old volunteer man to examine the presence of Dot cells in human blood. FIG. 4 shows that Dot cells were also present in the blood (m-Blood) and bone marrow (m-BM) of 4-week old mice. Dot cells were found in human blood (h-Blood). We further compared the ratio of Dot cells in E16.5 fetal, 4-week-old and 34 week-old mouse blood. The chart in FIG. 4 shows the fold of ratio of Dot cells in E16.5 fetal mice and 4-week-old mice compared to 34-week old mice. The isolation rate of Dot cells in the total blood of E16.5 fetal mice (0.46±0.029% of the total cells, n☐6) was about twenty times higher than that in 4-week old mice (0.023±0.002% of the total cells, n=4) and 25 times higher than that in 34-week old adult mice (0.02±0.001% of the total cells, n=3).

Figure 5:
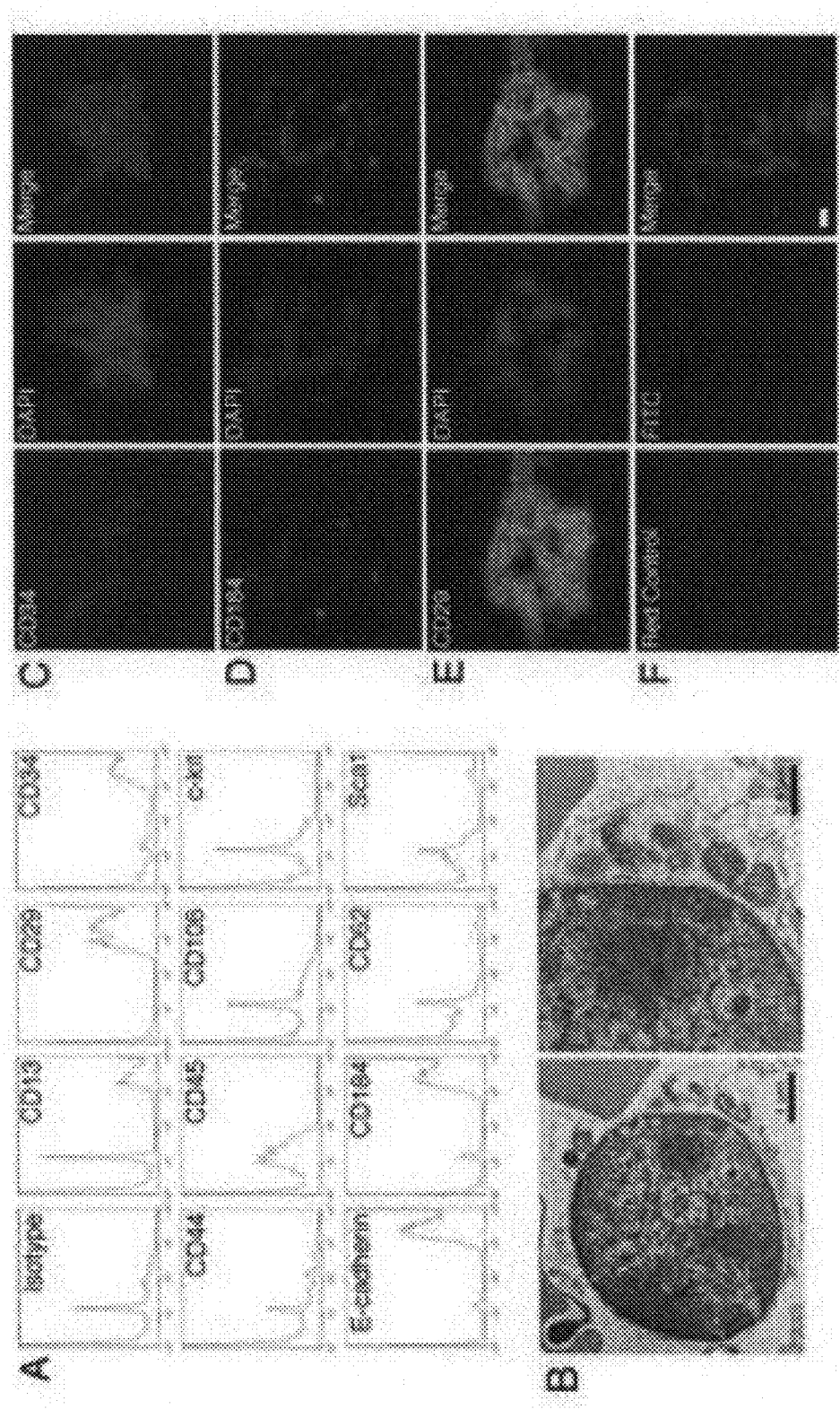
FIG. 5. Stem cell markers were expressed by Dot cells. 5A shows the expression of stem cell markers on Dot cells using FACS analysis. Freshly E-cadherin sorted cells were reacted with other stem cell marker antibodies, as described in the methods section. The expression of each marker was analyzed using FlowJo software. More than 85% of Dot cells express integrin β1 and CD184. About 50% of cells express CD34, and 15% express CD13. The detailed morphology of Dot cells was also examined using electron microscope. 5B shows a sorted Dot cell, 5 µm in diameter, having a large nucleus but small cytoplasm. This cell also shows some intracellular organelles, but no significant cytoplasm components. The stem cells marker expression on Dot cells was also examined using immunofluorescent stain by a confocal microscopy (FIG. 5C-F). Dot cells are positive for expression of CD34, CD184 and integrin β1. Bar=10 µm.

Dot cells also express integrin β1, CD34 and CD184. To further characterize the surface markers of Dot cells, sorted Dot cells were examined by FACS analysis. FIG. 5A shows that Dot cells also expressed integrin β1 (CD29), partly CD34 (50-60%), CD184. About 15% of Dot cells also expressed CD13 and few of them (~5%) expressed Sca1. However, Dot cells did not express CD45, CD44 and CD117 (c-kit). Dot cells were cultured on cover slides and their surface marker expression was further examined using immunofluorescent staining and a confocal microscopy. FIG. 5B shows an electron microscopy image of a Dot cell that was freshly sorted. This cell was about 5 µm in diameter and had a large nucleus with few cellular organelles and almost no cytoplasmic components. Cultured Dot cells were stained with integrin β1, CD34 and CD184 (FIG. 5C). Integrin β1 stained as rod shape on Dot cells.

Figure 6:
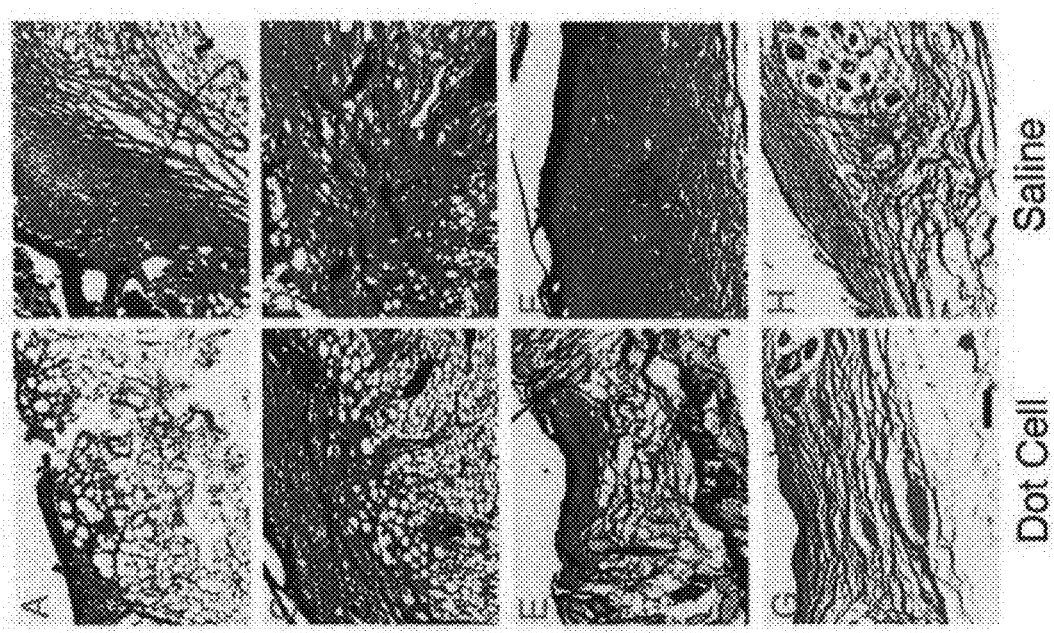
FIG. 6. The wound repair function of Dot cells. $5 \times 10^5$ freshly sorted Dot cells in 100 µl saline were introduced into each dorsal skin wounded adult mouse through tail vein injection. Wounds were collected from Dot cell transplanted mice on day 5 (A), day 7 (C), day 15 (E) and day 20 (G). The wounds of the saline injection control group were collected on the same days (B, D, E, H). Fibrotic tissue expression in wounds was examined using trichrome stain, and the images were taken using a conventional microscopy with bright field light. Bar=400 µm.

Transplantation of Dot cells to wounded adult mice reduces scar. The effects of Dot cells on postnatal wound repair were examined. Five hundred thousand freshly sorted E16.5 Dot cells in 100 µl saline were injected to each wounded postnatal mouse through its tail vein. FIG. 6 shows trichrome stained wound sections collected on day 5 (A), day 7 (C), day 15 (E) and day 20 (G) after Dot cell-transplantation. The wounds in saline injected control group were collected on the same days (B, D, E, H). Images were taken with a conventional microscopy with bright field light. Significantly less scar tissue was observed in the Dot cell-transplanted group. In addition, control E16.5, passage 3, dermal fibroblasts were transplanted via tail vein injection into wounded adult mice. This group had similar scarring as the saline control group.

Figure 7:
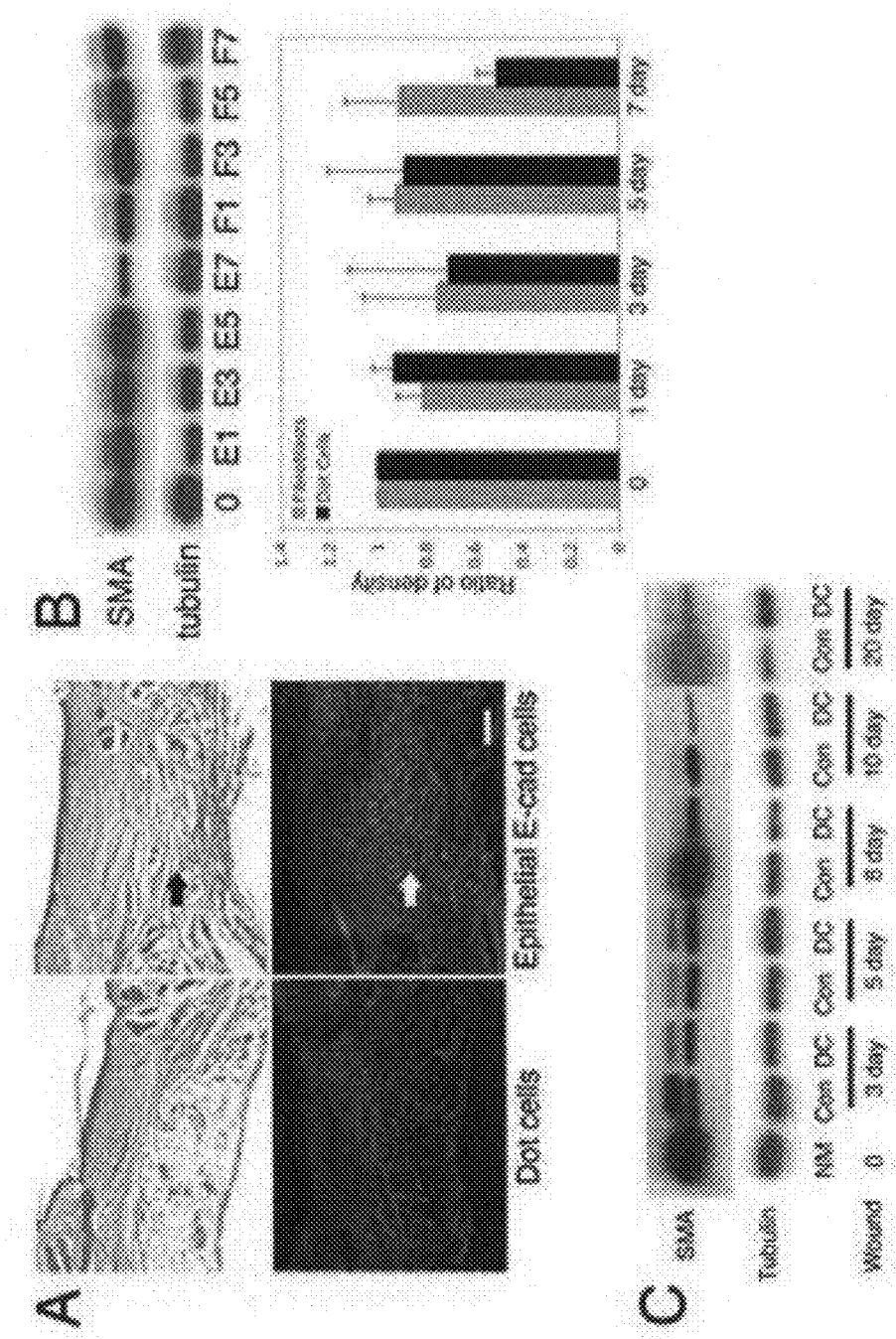
FIG. 7. The expression of type-I collagen and SMA in wounds. $5 \times 10^5$ E-cadherin positive cells sorted from skin of postnatal mice or $5 \times 10^5$ Dot cells were transplanted into each wounded mouse. Wounds were collected and sections were stained with H&E or type-I collagen antibody. 7A shows images for H&E stain (upper panel) and fluorescent FITC-labeled collagen expression (lower panel). Less fibrotic tissue and less collagen expression was observed in Dot cell transplanted wounds (left panel) compared to postnatal skin E-cadherin positive cells transplanted wounds (right panel). Bar=400 µm. 7B shows immunoblot of SMA expression in the Dot cell transplanted group from day 1 to day 7 (E1-E7) wounds versus E16.5 fetal fibroblasts transplanted wounds (F1-F7). Decreased SMA was detected in Dot cell transplanted group on day 7 (E7). The densitometry analysis of two separated immunoblot experiments demonstrate a decreased expression of SMA in Dot cell transplanted wounds on day 7.

Dot cell-transplanted wounds express less type-I collagen and smooth muscle actin. Five hundred thousand epithelial E-cadherin positive cells isolated by FACS from postnatal mice skin were transplanted to each wounded adult mouse, and compared to Dot cell-transplanted wounds. FIG. 7A shows both H&E stain and immunofluorescentlabeled collagen expression on 8-day wounds. Less fibrotic tissue and less collagen were observed in the Dot cell-transplanted wounds compared to the epithelial E-cadherin positive cell transplanted wounds; the repaired dermal tissue formed a reticular network structure in the Dot cell-transplanted wounds. Because smooth muscle actin (SMA) is expressed by myofibroblasts that release interstitial collagen and exhibit strong contraction ability and scarring, the expression of SMA in the wounded tissue was examined using immunoblot in wounds collected from E16.5 Dot cell-transplanted (E1-E7) and fibroblast-transplanted (F1-F7) groups (FIG. 7B). Lower SMA expression in Dot cell-transplanted wounds was detected on day 7 in two separated groups (FIG. 7C). Also postnatal Dot cells, collected from adult mouse blood, were transplanted to wounded mice. The expression of SMA in wounds from Dot cell-transplanted (DC) was compared to saline-injected groups (con), and significantly decreased SMA expression was detected from 8 day and later (FIG. 7D).

Figure 8:
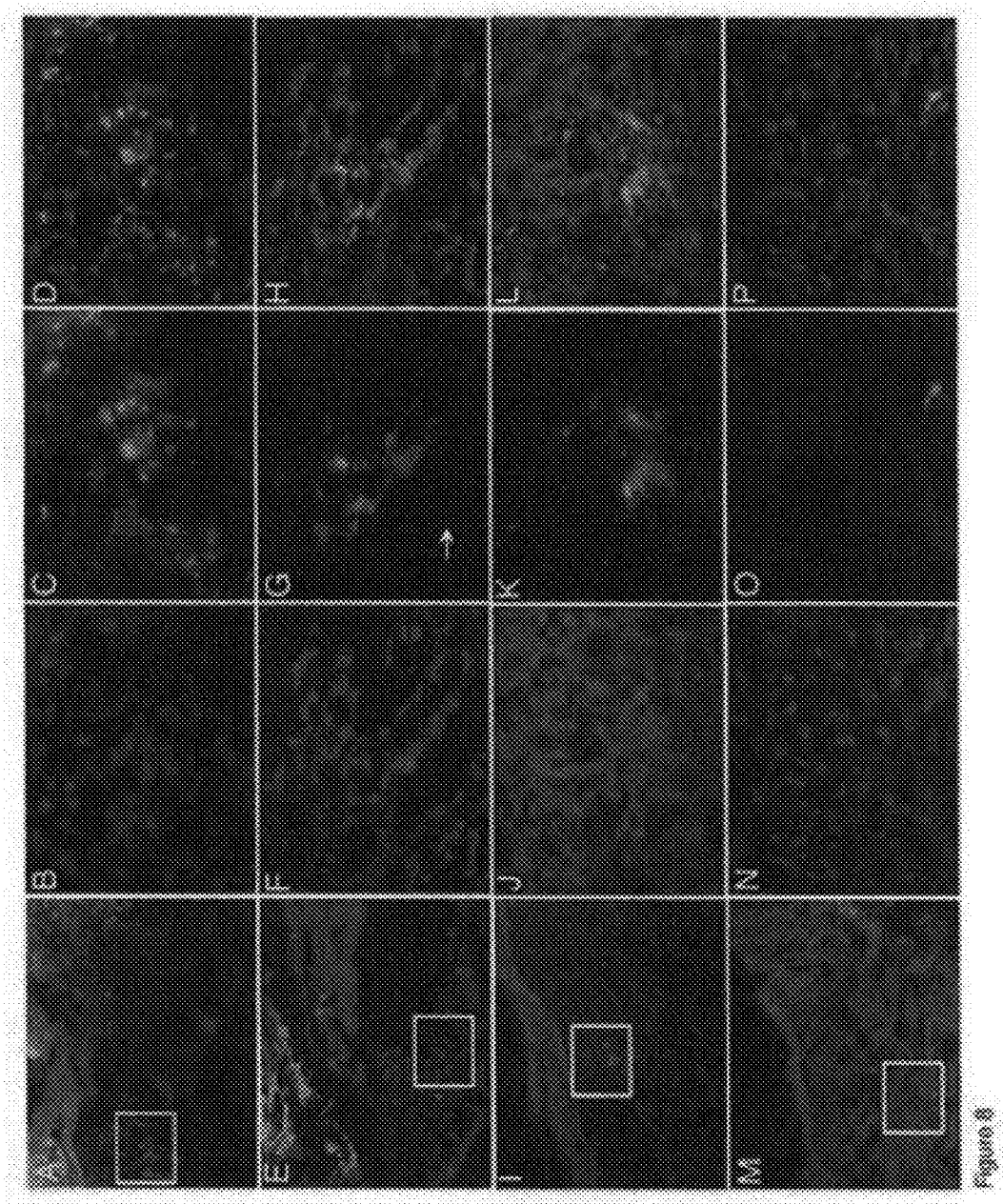
FIG. 8. Dot cells repair wounded dermal tissue. Five hundred thousand Dot cells freshly sorted from E16.5 GFP fetuses were transplanted to each wounded Balb/C adult mouse. Wounds were collected on day 1 (A-D), day 3 (E-H), day 7 (I-L) and day 15 (M-P) after wounding. The images in B-D, F-H, J-L and N-P were the enlargement of the square images in A, E, M, and I respectively. In 1 and 3-day wounds, GFP cells were located at the edge of the damaged area. By day 7, when the re-epithelialization was finished and major dermal structure was recovered, GFP cells were located at the center of wounds. After 15 days, only a small number of GFP positive cells can be seen. The restored tissue showed very weak GFP expression.

Dot cells restore dermal tissue and blood vessels. The location of transplanted Dot cells in wounds was examined using E16.5 Dot cells freshly isolated from GFP-transgenic mice (FIG. 8). On day 1, GFP-labeled cells were observed at both sides of the wound (8A-8D). The majority of bright GFP-staining cells are small in size. However, some bright GFP stained large cells can also observed in wounds, indicating these cells are differentiate dermal cells. On day 3, GFP cells were detected in the dermal wound bed (8E-8H) and a GFP-positive circle could also be detected (arrow in 8G), indicating Dot cells also can differentiate to blood vessel in wounds. On day 7, wounds had reepithelialized, and the newly formed dermis had a reticular cellular network structure; GFP cells were found mainly at the center of the wound bed, indicating the center area was not fully repaired (8I-8L). By day 15 (8M-8P), when the wound defects were totally repaired, few small GFP-labeled Dot cells were detected. However, the majority of differentiated dermal cells in wounds still weakly express GFP.

Figure 9:
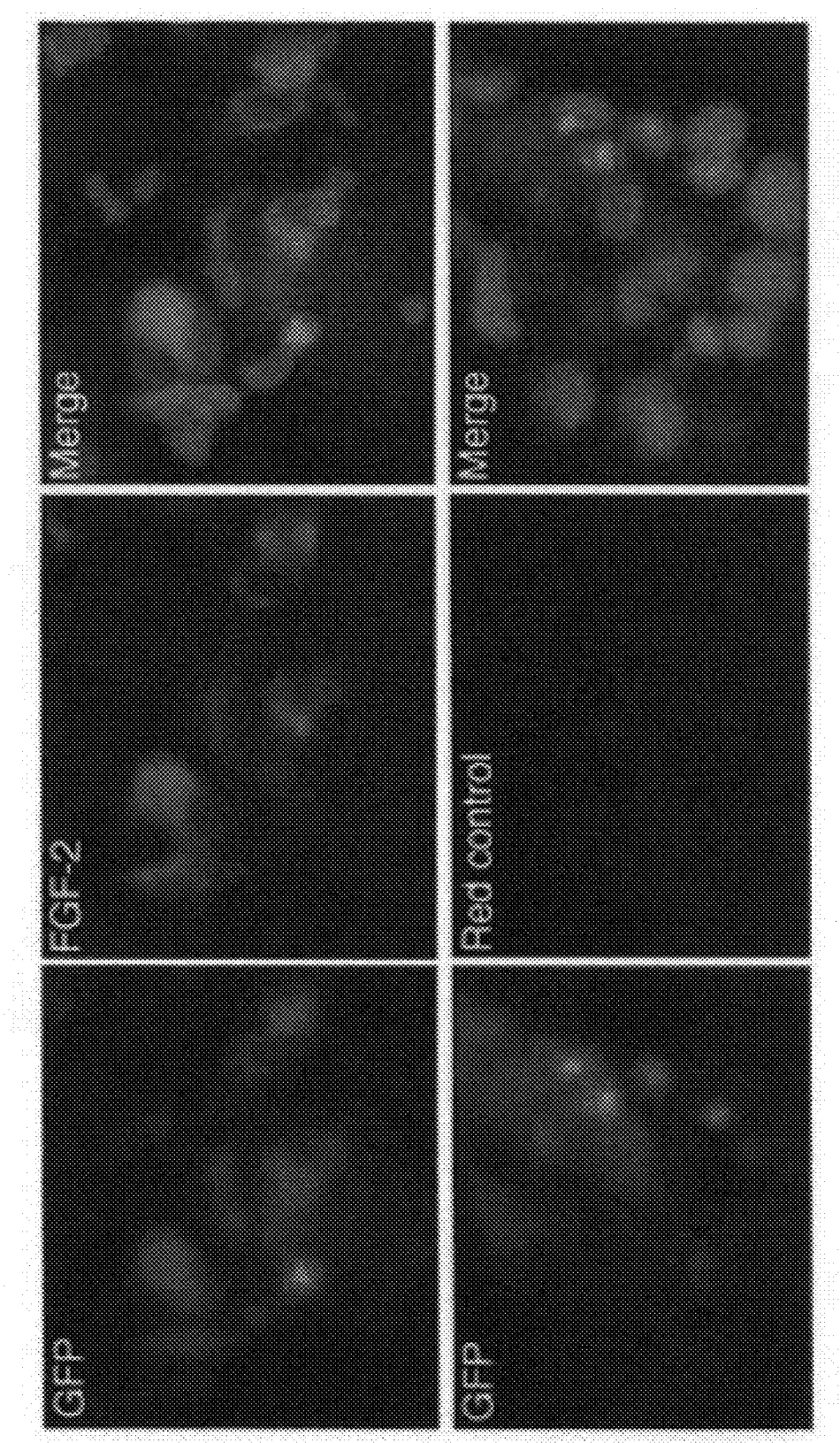
FIG. 9. Dermal cells derived from Dot cells express FGF-2 at high levels. FGF-2 expression was examined using fluorescent staining on 7-day wounds from transplantation of GFP-labeled Dot cells. Strongly GFP positive cells that were smaller did not show FGF-2 expression. However, the majority of large differentiated cells expressed FGF-2 (red) and weak GFP.

Differentiated Dot cells express strongly to FGF-2. The mechanism of scarless function of Dot cells was further examined through their FGF-2 expression, because FGF-2 is antagonist to fibrosis through its function of inducing cell proliferation and decreasing cell differentiation. FIG. 9 shows the immunofluorescent stain for FGF-2 (red) in 7-day wound sections. These wounds were collected from GFP-labeled Dot cells transplanted mice. Some bright GFP-labeled smaller cells do not express FGF-2, however, the differentiated larger cells that expressed relatively weaker GFP were coexpressing FGF-2. These data indicate that dermal repaired cells were derived from differentiation of Dot cells; Dot cells do not express FGF-2 before they were differentiated.

In the present study, we introduce a group of new cells. Due to their tiny dot shape, these small cells were named Dot cells. Dot cells are detected from blood of both fetal and adult mice. We believe that Dot cells are an unidentified group of cells since there are no previous published reports describing their similar cell morphology or specific stem cell markers. Dot cells express strongly to E-cadherin, integrin β1, CD184, partially to CD34, CD13 and low to Sca1. E-cadherin is mainly expressed by epithelial cells, and integrin β1 is a well-known epidermal stem cell marker. The strong expression of both E-cadherin and integrin 1 μl on Dot cells in normal E16.5 mouse skin indicates that these cells are targeted to epidermal development.

Due to their unusually small size and their strong expression of stem cell markers such as E-cadherin, integrin β1 and CD34, Dot cells are believed to be primitive cells. Our data clearly demonstrate that Dot cells have strong homing effects for tissue regeneration. They specifically migrate to wounds and differentiate into dermal cells that release less interstitial collagen and therefore, produce less scar.

We believe that the mechanism for Dot cell migration to the damaged area is via the membrane presence of CD184, a seven-transmembrane G-protein coupled receptor. CD184 functions as a receptor for stromal cell-derived factor-1 (SDF-1), an important chemokine for heart development and stem cell migration. The release of SDF-1 can be upregulated when tissue is damaged, which leads to the homing of circulated stem cell. The fibroblast-transplanted group did not show the same scarless repair effect as seen with the Dot cell-transplanted group. This indicates that transplanted fibroblasts do not home to damaged tissue.

Our data also demonstrate that the tissue repair effect of Dot cells is through a result of their accelerated differentiation into dermal cells and blood vessels at the wound site. The population of regenerated dermal cells in the scarless healing wound results from the rapid differentiation of homing Dot cells (FIG. 8).

We used Dot cell-transplantation method instead of topical application of Dot cells to the wound bed in our experiments. Because Dot cells are blood-derived and very small, it is easier and more physiological to apply them through circulation. In addition, blood-transplantation is easier to control the cell numbers without losing cells Dot cell-derived dermal cells express strongly FGF-2, a growth factor that induces proliferation of these fibroblasts. In addition, FGF-2 also reduces the cell differentiation effects of local latent TGF-β; and subsequently reduces the differentiation of fibroblasts into myofibroblasts. Myofibroblasts release large amounts of interstitial collagens and induce strong tissue contraction, i.e. resulting scar formation.

Because all the experimental wounds were 6 mm in diameter, only a small of accelerated wound healing by Dot cells is detected. However, Dot cells can also increase healing speed, and may help in the healing of diabetic wounds.

The effects of Dot cells on scarless wound healing mainly occur in the early stages after the initial injury. We have observed that scarring is reduced in saline control wounds after day 20 when there were no significant differences of scarring between Dot cells and saline injected wounds. Reduced scarring in control group on 20 day wounds may be explained by the result of host stem cells that migrate from blood or BM and contribute to wounds healing.

We have found that the ratio of Dot cells in E16.5 fetal mice is more than twenty times higher than that of adult mice, indicating that Dot cells are the key for scarless healing. To confirm that higher Dot cell number augments tissue repair, we transplanted 500,000 isolated Dot cells into each wounded adult mouse. The cells number for the transplantation were calculated as about 40% of total Dot cells of one recipient animal, i.e. 1.5 (volume of blood in one mouse)×4×$10^9$ (total blood cells per ml)×0.02% (the ratio of Dot cells in total blood cells)=500,000. Our data indicates that a 40% increase in the number of Dot cells can induce scarless healing. The ratio of Dot cells in E16.5 fetal mice is twenty times higher than that of adult mice.

In the transplantation model, we found that GFP-labeled Dot cells lose their GFP expression after the dermal structure is fully restored. This suggests that the renewal of Dot cells population is well regulated. This self-regulation can effectively limit cell proliferation rate in vivo and prevent hyperproliferation of transplanted stem cells to become 'cancer stem cells' in recipients.

Our data provide evidence that Dot cells play a major role in regenerating the injured dermis and reducing scar formation. We believe that a high number of circulating Dot cells is the key for fetal scarless wound healing. In contrast, scarring in adults is a result of fewer circulating of Dot cells.

Example 2

Dot Cells: Primitive Marrow and Circulating Regenerative Fusogenic Cells

We have herein identified a novel group of circulating and bone-marrow-derived DNA and protein positive particles and termed them "Dot cells". The morphology of blood-derived Dot cells does not match the definition of conventional eukaryotic cells. Their size ranges from 0.1 to 2 μm, and they do not have nuclear membrane or intracellular organelles. Blood-derived Dot cells have a unique self-renewal mechanism by release of grouped new Dot cells from colonies. When present with differentiated cells, Dot cells aggregate and fuse together. The fused aggregates then undergo cellular transdifferentiation. Both the nuclear and cytoplasmic components of the newly differentiated cells are derived from Dot cell fusion. In vitro expanded Dot cells form spheroids, which release fused or grouped Dot cells that contribute to tissue regeneration during in vivo wound healing. Dot cells are a newly identified cellular population in bone marrow and blood that forms eukaryotic cells by self-fusion.

We isolated a group of E-cadherin-positive small dot-shaped cells from mouse blood, and from human blood, which we termed "Dot cells". The ratio of Dot cells in fetal mouse blood is more than twenty times higher than in the adult. Hematogenously transplanted, freshly isolated Dot cells regenerate skin wounds and reduce scar formation in postnatal mice. Dot cells strongly express E-cadherin, integrin, β1/CD29, CD184/CXCR4, CD34, CD13 (low) and Sca1 (low). Freshly isolated Dot cells do not express CD45 or CD117/ckit.

Here we provide new evidence that Dot cells do not fit the definition for true eukaryotic cells. Their average size is about 0.5 μm. They do not have nuclear membrane or intracellular organelles. Pure Dot cells have a unique rapid self-renewal pattern in culture, which is not through mitotic division. In vitro expanded, blood-derived, Dot cells retain their regenerative activity during skin wound healing. Dot cells aggregate and fuse together before undergoing cellular transdifferentiation. Fused Dot cells contribute to the formation of both nuclear and cytoplasmic domains of the differentiated cells. The fusion pattern and lineage differentiation of Dot cells are determined by the lineage of the co-present differentiated cells. Our data provide evidence that circulating tissue progenitor cells are produced by the fusion of Dot cells.

Unique morphology and self-renewal pattern of Dot cells. The detailed morphology of freshly sorted (FIG. 10A) and cultured, blood-derived, Dot cells (FIG. 10B) was examined by electron microscopy (EM). Cultured Dot cells range in size from 0.1 μm to 2 μm, but freshly sorted Dot cells are about 0.5 μm. Dot cells have a bi-layer outer membrane and a variety of shapes. Some Dot cells have a homogenous cytoplasmic component and others contain a unique organelle pattern. Dot cells do not fit the definition of true eukaryotic cells as they do not have a nuclear membrane. The variety of Dot cell shapes suggests that Dot cells are either a mixed population or undergo maturation from a simple uniform structure to the more complicated structures.

Figure 10:
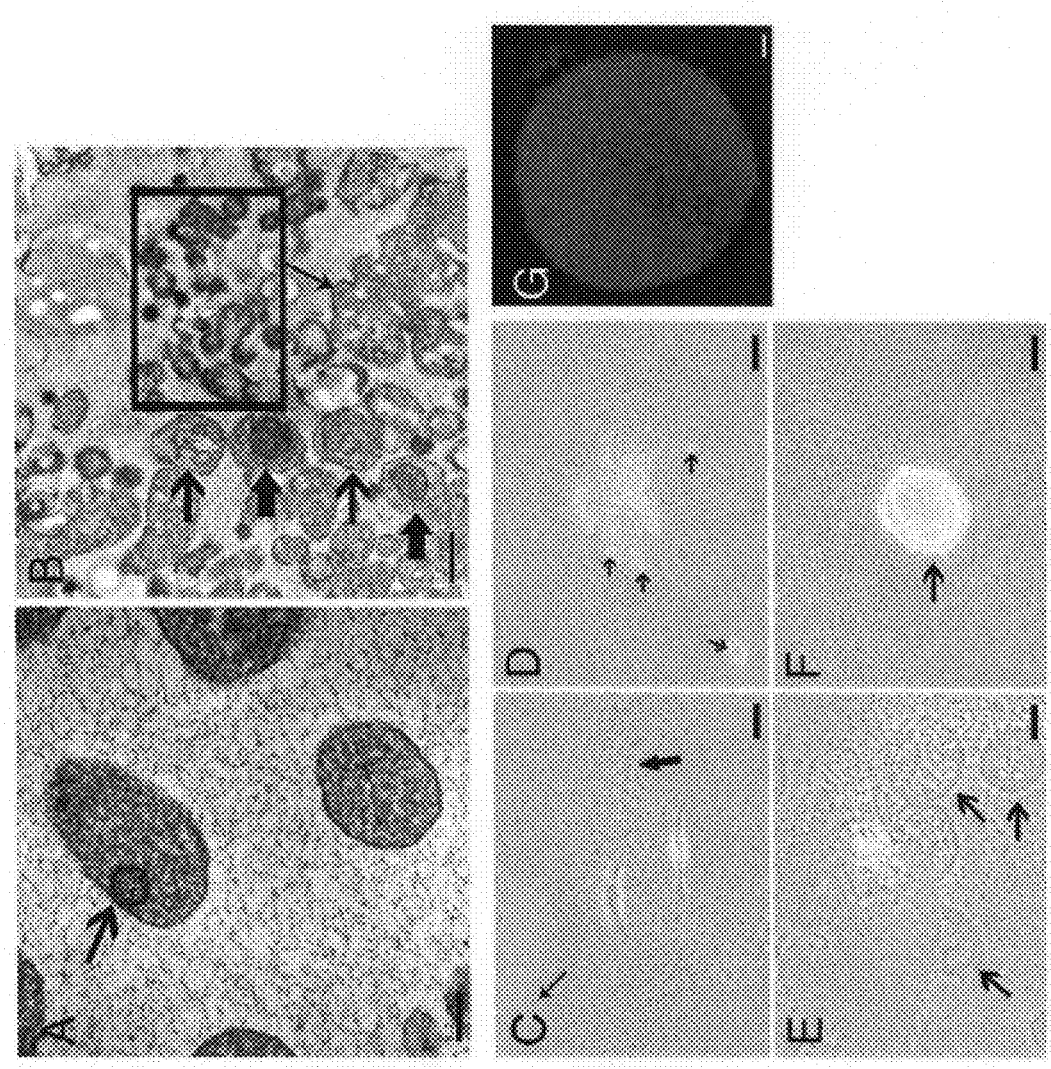
FIG. 10. The unique morphology and replication pattern of Dot cells. (A) EM image of two freshly isolated blood-derived Dot cells with a 0.5 µm diameter and a bi-layer membrane. A small dense organelle is inside one Dot cell (arrow); (B) Cultured blood derived Dot cells have a variety of shapes. Some are about 0.1-0.3 µm in diameter with a dense EM stain (inside the square). Some have a fused shape (thin arrow), some have a mitochondria-like organelle inside (thick arrows), and some have multiple circular structures inside (solid arrows). Dot cells were sorted using E-cadherin antibody from adult mouse blood and then cultured in (MEM with 20% FBS. (C) Dot cells have a unique "dot" morphology, when they reach confluence, individual Dot cells become indistinguishable due to their tight cell-cell connections. The individual Dot cells show larger (thick arrow) and small (thin arrow) in sizes. (D) When Dot cells reach confluence, a large spheroid forms on top of the monolayer. This spheroid constantly releases grouped Dot cells (arrows) that migrate away. (E) The self-renewal of Dot cells is not through mitotic division. Dot cells form a circular shape (arrows) and constantly released from the colony. (F) A large spheroid is located on top of the Dot cell monolayer. No visible Dot cells are released from this spheroid, but a shell-like structure can be seen at the outer layer of this spheroid. (G) A merged confocal image of a cultured spheroid, which is composed of numerous small bodies of DAPI positive nuclear material. Bars in 1A=0.2 µm, in 1B=0.5 µm. Bars in 1C-1F=40 µm. Bar in 1G=10 µm.

In addition, we have found that blood-derived Dot cells isolated from GFP-transgenic mice express many surface proteins, but do not express GFP, which is induced by β-actin promoters. GFP expression on Dot cells appears only when the activation of fusion is initiated. These results demonstrate that Dot cells are primitive cells. Blood-derived Dot cells have a unique self-renewal pattern in vitro (FIG. 10C to 10F). Initially, Dot cells have a small "dot" morphology, however at confluence, individual Dot cells become indistinguishable due to their tight cell-cell connections. Some Dot cells are larger (thick arrow) and some are smaller (thin arrow) in cultural plate. Two small mesenchymal-like cells are present in the image for the size comparison with Dot cells (FIG. 10C).

The self-renewal of cultured Dot cells is unique. When Dot cells become confluent in culture, large spheroids form on top of the monolayer, which release grouped Dot cells (arrows in FIG. 10D). However, before Dot cells reach confluence, multiple newly produced Dot cells are released from the large colony and rapidly spread in the culture plate (FIG. 10E). These circular masses of Dot cells migrate away from the colony. The self-renewal patterns of cultured blood-derived Dot cells indicate an unknown replication but not a mitotic cell division mechanism. Dot cells also form large spheroids, as has been described for embryonic stem cells. FIG. 10F shows a large spheroid on top of the confluent Dot cell monolayer. A shell-like structure comprises the outer layer of this spheroid. Multiple un-attached (white dots) and attached (dark dots) Dot cells are in the background. Due to the small size of Dot cells, it is difficult to distinguish the detailed morphology of the cultured spheroids.

FIG. 10G shows a merged confocal image of a cultured spheroid. Although Dot cells do not have a nuclear membrane, they stain positive to DAPI. The spheroid is composed of numerous small bodies of DAPI-positive nuclear material. Almost all the nuclear material has a small particle shape, suggesting that is the DNA or RNA material of a single Dot cell. Merged confocal images of a DAPI-stained Dot cell spheroid shows many large DAPI-positive nuclear material bodies located on the outer surface of this spheroid, suggesting they are fused nuclear materials of Dot cells. Again, numerous small DAPI positive materials are located inside of this spheroid, suggesting they are the nuclear particles from individual Dot cells. A shell-like structure has also been observed at the outer layer of this spheroid, similar to the structure observed in FIG. 10F.

Aggregated Dot cells fuse slowly in vitro. To understand the mechanism of Dot cell differentiation, blood-derived Dot cells were cultured and monitored to follow their fusion and differentiation patterns. The same group of Dot cells was monitored daily for 18 days and the images were taken with bright field microscopy. After 18 days, only the number of aggregated Dot cells increased, but the morphology of the aggregations had almost no change. Dot cells in the center of the aggregate were denser, but did not fuse after 18 days. Two groups of aggregated Dot cells with many scattered Dot cells in the background after one month in culture. One of the aggregates showed a faint membranous structure forming at one side while the other aggregate did not show any sign of fusion. These data demonstrated that fusion of Dot cells is slow when in the absence of differentiated cells.

Figure 11:
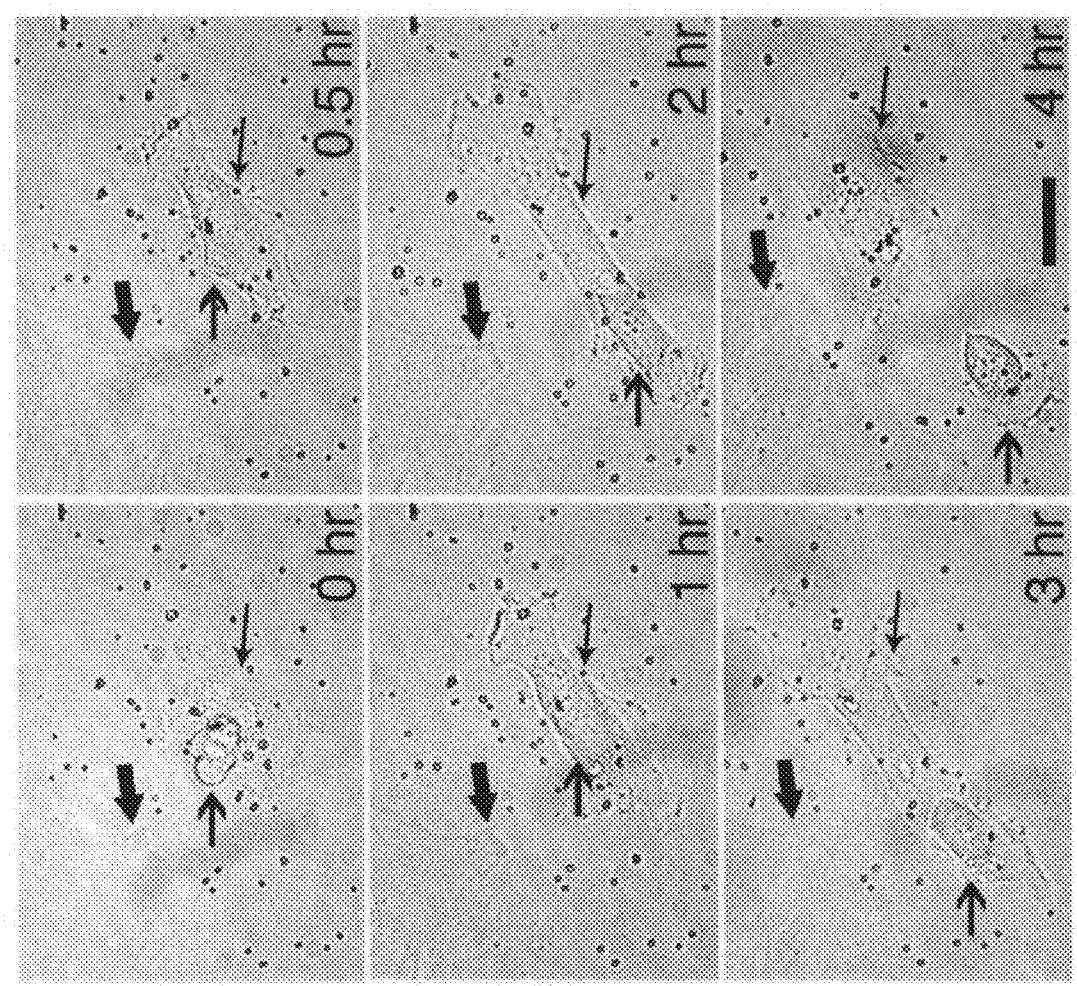
FIG. 11. Cultured Dot cells aggregate, fuse, and further differentiate into eukaryotic cells. Dermal fibroblasts were cultured to 10% confluence. Ten million blood Dot cells were then added to each 100 mm plate. After one week, the fusion-differentiation of Dot cells was examined using an inverted bright field microscopy. Still images of a time-lapse study show that at time 0, a group of aggregated Dot cells (thin arrow) were settled near a fibroblast (thick arrow pointing to the membrane of a fibroblast). A small spheroid (wide arrow) is located on top of the aggregated dot cells. The aggregated Dot cells quickly fuse, with a distinct membrane structure appearing at the outer edge by 30 min. At 4 hours, the aggregate becomes a differentiated cell; meanwhile the small spheroid also differentiates to a cell shape and is separated from the aggregation-derived cell. Bar=40 µm.

Differentiated cells are required for inducing Dot cell self-fusion. Although the in vitro spontaneous differentiation of Dot cells can be as slow as days to months, we found that Dot cells differentiate rapidly in vivo during skin wound repair (Kong et al. (2008) Exp Cell Res 314, 1529). This suggests that the differentiation of Dot cells in vivo is regulated by the wound microenvironment. Although chemically regulated lineage differentiation has been described for stem cells, we have not been able to induce Dot cell differentiation using either growth factors or chemicals. Instead, we find that Dot cell fusion differentiation can be induced when Dot cells are co-present with differentiated cells. Mouse skin fibroblasts (100,000) were cultured on a 100 mm plate, and blood-derived Dot cells were added one day later. Dot cells quickly aggregated when they had physical contact or were located adjacent to fibroblasts. Soon after the aggregation, membrane fusion occurred in the outer edge of the aggregated Dot cells. FIG. 11 shows still images of a time-lapse study of Dot cell fusion-differentiation in the presence of fibroblasts taken by bright field microscopy. Dot cells aggregate and fuse in 30 minutes, and obtain a cellular morphology within 4 hours. Multiple Dot cells fuse to become one differentiated cell or become a small progenitor cell (newly fused cells are significantly smaller than the differentiated cells). The fusion-differentiation process happens rapidly, and therefore, elucidation of the exact morphology and transitional time for progenitor cell formation is difficult.

In order to understand if the co-culture-induced Dot cell fusion-differentiation occurs through physical contact with the differentiated cells or from unknown biochemicals released from the differentiated cells, the insert chamber co-culture method was used. We found that when blood-derived Dot cells are co-cultured with differentiated cells in the same environment but different chambers, only Dot cells that migrate into the differentiated cell chamber fuse and differentiate. Dot cells remained in their original chamber replicate but do not differentiate. These observations suggest that the fusion-differentiation of Dot cells is induced either by physical contact with the differentiated cells or by organelles released from the differentiated cells. Secreted factors alone do not induce blood-derived Dot cell differentiation. We also found more cultured BM-derived Dot cells in a fused morphology than cultured blood-derived Dot cells. This suggests that the majority of BM Dot cells are fused before migrating into the blood. In cultured BM-derived Dot cells, within 2 days, each fused group becomes a small cell. Individual Dot cells can still be found in the background of the grouped cell masses and the small newly differentiated cells.

Due to the difficulty of observing the aggregation and fusion of living Dot cells, we used high magnification confocal microscopy. Four groups of aggregated blood-derived Dot cells, stained with DAPI, were examined under a 100× lens, with 2× or higher zooms of confocal microscopy. Both the nuclear area and cytoplasmic area are derived through Dot cell fusion.

Figure 12:
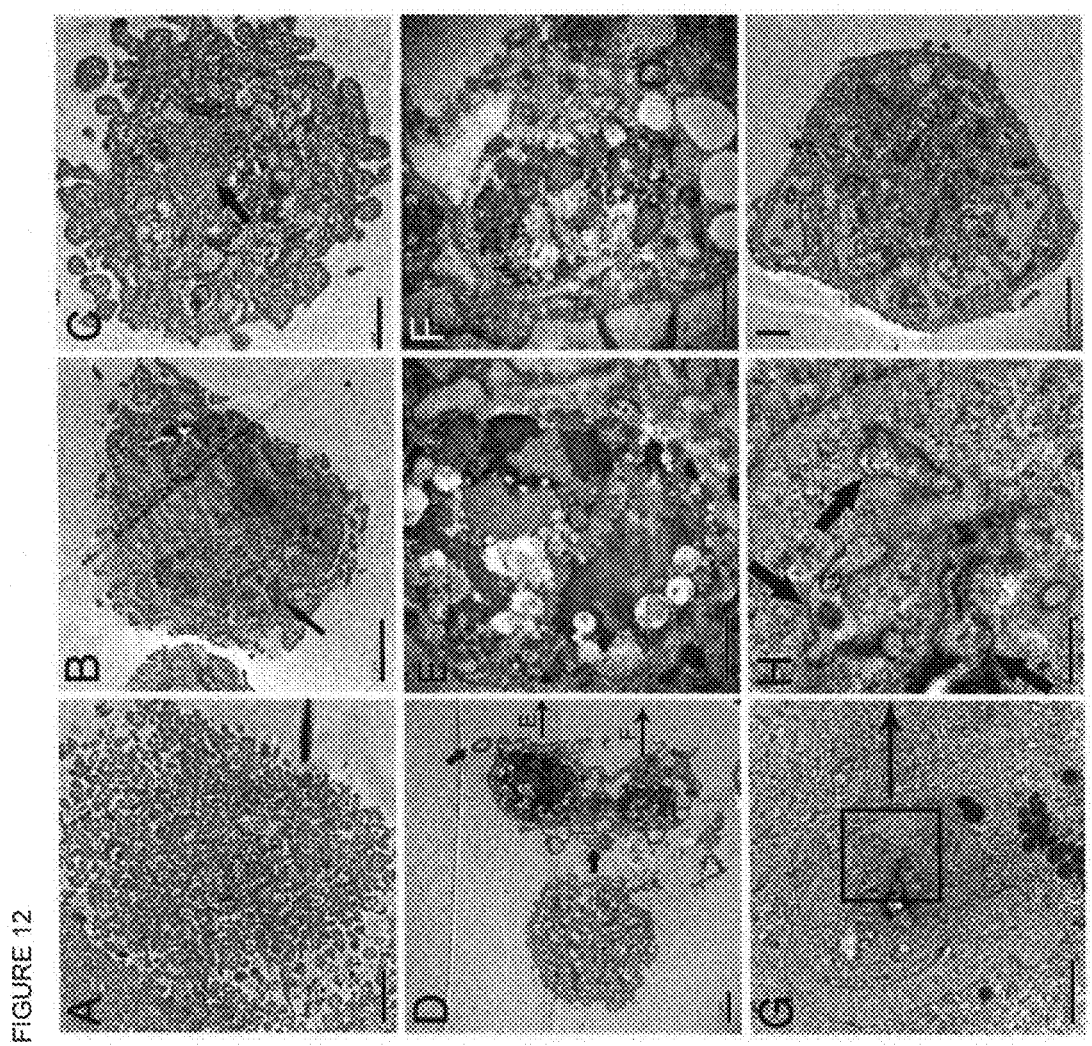
FIG. 12. Both the cytoplasmic and nuclear domains of differentiated cells are derived from Dot cell self-fusion. Mouse or rat Dot cells were co-cultured with mouse or rat fibroblasts for 5 days and the cells scraped off for EM analysis. (A) An aggregate with more Dot cells located in the center than in the peripheral area. Fusion at the outer edges of this aggregate has not yet occurred. (B) A fused cell with a nucleus and membrane. Dot cells are located in the cytoplasmic area. (C) A group of fused Dot cells shows that the cellular membrane is formed by the Dot cell membranes. (D) EM of two fusion derived differentiated cells, the right cell has nuclear-like structures composed of numerous dense particles. A nuclear membrane structure is present at the outer border of the nuclear-like structures. In addition, several Dot cells are observed outside of these two fusion-derived cells (thick arrows). (E to F) The enlarged images of the upper and the lower nuclear-like structures in D show numerous Dot cells. (G) A fusion-derived mouse cell has distinguishable nuclear membrane and intracellular organelles. (H) The image of the enlarged area from G shows several Dot cells (thick arrows) inside the nucleus. (I) Another Dot cell fusion-derived cell has a cytoplasmic membrane but no nuclear membrane. Again, numerous Dot cells are present within this cell.

EM images demonstrate the fusion of both mouse (FIG. 12A, 12G, 12H) and rat (FIG. 12B-12F, 12I) blood-derived Dot cells. FIG. 12A shows a group of aggregated Dot cells, in which the Dot cells are about 0.5 µm. Although this aggregate has formed a cellular figure, it does not have nuclear and cytoplasmic membranes. The cytoplasmic component of the newly differentiated cell is derived by multiple Dot cell fusions (arrow in FIG. 12B). FIG. 12C shows a group of fused Dot cells. Although fiber-like structure has appeared in the center of this cell (arrow), indicating it will become the final nuclear material, the nuclear membrane has not formed. Also, the cellular membrane of this cell is in the formation by membrane fusion of multiple Dot cells. FIG. 12D shows two newly fused cells Multiple Dot cells are located in the nuclear areas of the new cell on the right under higher magnification (FIG. 12E, 12F). Although the nuclear membrane has formed, some Dot cells can still be identified inside the nuclear membrane (FIG. 12G, 12H). FIG. 12I shows a newly fusion-derived cell, which, although has a cellular membrane, has not yet formed a nucleus. These data demonstrate that both the cytoplasmic and nuclear domains of the differentiated cells are derived from Dot cell self-fusion.

The mechanism of Dot cell aggregation and subsequent self-fusion could be due to their strong expression of E-cadherin and CXCR4/CD184. E-cadherin is a transmembrane protein on epithelial cells. E-cadherin also facilities the aggregation and fusion of cytotrophoblasts into terminal differentiated multinucleated syncytial trophoblasts. CD184, also termed fusin/CXCR-4, is a seven-transmembrane, G-protein coupled receptor that is necessary for the entry of the human immunodeficiency virus (HIV) through fusion into target cells.

Figure 13:
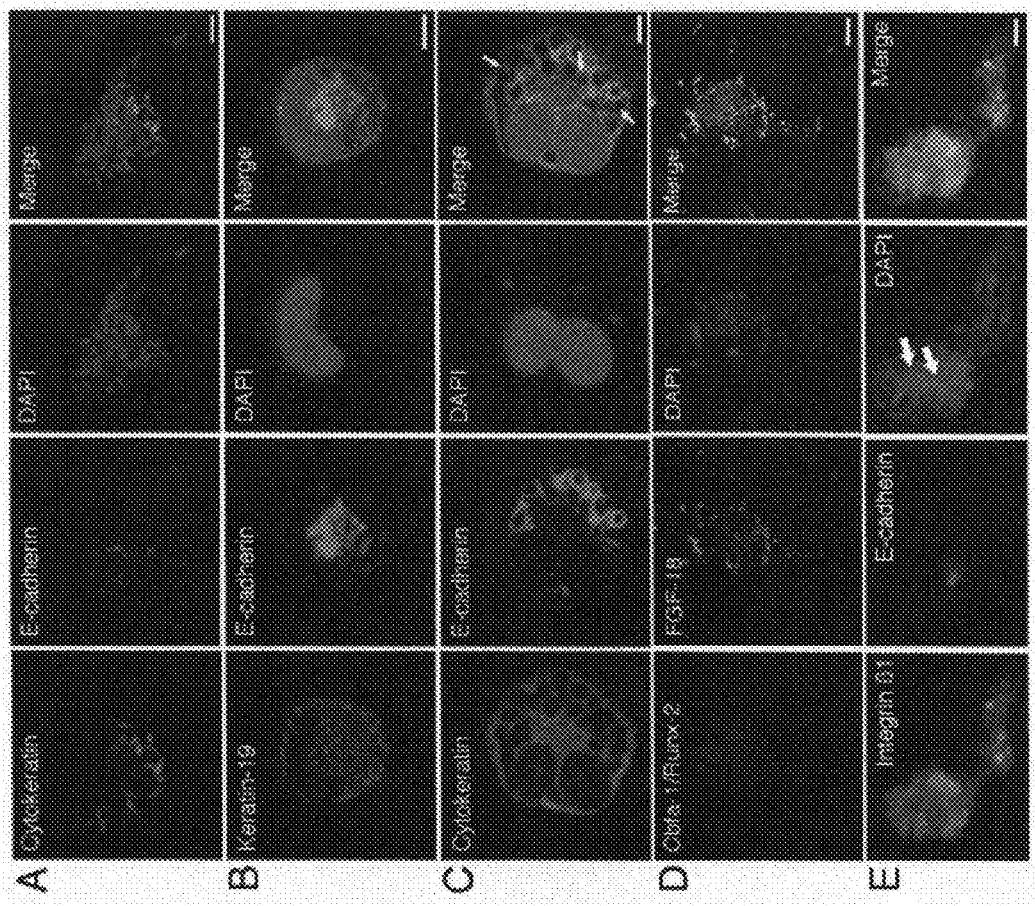
FIG. 13. Dot cells differentiate into epithelial and mesenchymal cells. Blood Dot cells were co-cultured with epidermal cells and confocal images were taken to examine the pattern of Dot cell differentiation. (A) In an aggregate, the majority of Dot cells express E-cadherin but some Dot cells express cytokeratin. No co-localization of E-cadherin and cytokeratin was found in single Dot cells. (B to C) Both keratin-19 and cytokeratin are expressed in a diffuse pattern while E-cadherin is expressed as small red circles inside the cells. Although both cells have two nuclei, some DAPI stain is still detectable inside some red circles (arrows in C). (D) The expression of Cbfa-1/Runx-2 and FGF-18 was examined in Dot cells after co-culture with osteoblasts. Confocal images show that Dot cells aggregate and form a mesenchymal cell shape, with Cbfa-1 expression inside the aggregate. FGF-18 is co-expressed with DAPI. (E) The expression of integrin β1 and E-cadherin was examined after co-culture with fibroblasts, using conventional fluorescent microscopy. Integrin β1 has a tubular shape to connect the aggregated Dot cells. Only a few cells express E-cadherin. DAPI staining shows that the DNA material of the aggregated Dot cells forms a cellular shape around both the border and center areas. The DNA staining in the center is denser. Bars in 4A to 4C=5 µm. Bars in 4D-4E=10 µm.

Dot cells self-fuse before differentiating into epithelial cells, cardiomyocytes, osteoblasts, and fibroblasts. Specific transcription factors have been used to reprogram somatic cells to multipotent stem cells. Expression of these factors by Dot cells was examined, and it was found that blood-derived Dot cells express Oct4, Nanog, and Sox-2. To determine if Dot cells have the ability to differentiate into multiple lineages, blood-derived Dot cells were co-cultured with epidermal cells, cardiomyocytes, MC3T3 cells (osteoblast cell line), and dermal fibroblasts, respectively. FIGS. 13A, 13B and 13C show the confocal images of Dot cell fusion-differentiation when co-cultured with epithelial cells. In one aggregate of Dot cells (FIG. 13A), the majority of Dot cells express E-cadherin but some Dot cells express cytokeratin. No co-localization of E-cadherin and cytokeratin occurred on single Dot cells. FIGS. 13B and 13C show the expression of keratin and E-cadherin in the fusion differentiation derived cells. Keratin is expressed in intracellular areas but not in Ecadherin positive areas, suggesting the keratin expression occurs after Dot cell-fusion and during differentiation. In addition, E-cadherin is expressed as small red circles inside the cells. DAPI positive staining is still detectable inside these circles (arrows in FIG. 13C). These observations suggest that the DAPI stain in each E-cadherin circle has a Dot cell origin.

Figures in 13D show confocal images of osteoblast differentiation of Dot cells. The expression of Cbfa-1/Runx-2 and FGF-18 was examined. Dot cells aggregate and form a cellular shape. Cbfa-1 does not colocalize with either FGF-18 or DAPI, however FGF-18 colocalizes with DAPI. Conventional microscopic images of fibroblast differentiation of Dot cells are shown in FIG. 13E. Integrin β1 has a tubular shape that connects the aggregated Dot cells. Only a few Dot cells express E-cadherin. The nuclear material of the aggregated Dot cells is arranged as a cellular shape around both the border and central areas. DAPI stain in the center is denser, suggesting these nuclear materials will further differentiate into the nucleus or nuclei of the final differentiated cell. Because the images were taken by conventional fluorescent microscopy, the DAPI stain of each Dot cell was denser compared to those taken by confocal microscopy. In vitro co-culture studies demonstrate that Dot cells fusion-differentiate into epithelial cells, osteoblasts and fibroblasts. In addition, after co-culture with cardiomyocytes, Dot cell fusion-derived cells express the cardiomyocyte markers troponin-I and connexin-43. The control immunostaining groups did not show any positive stains. These results suggest that Dot cells have multi-lineage differentiation potential and their lineage is determined by the lineage of the co-present cells. Moreover, unlike embryonic stem cells or genetically altered stem cells, Dot cells do not form teratomas in nude mice by 10 weeks after subcutaneous injection.

Figure 14:
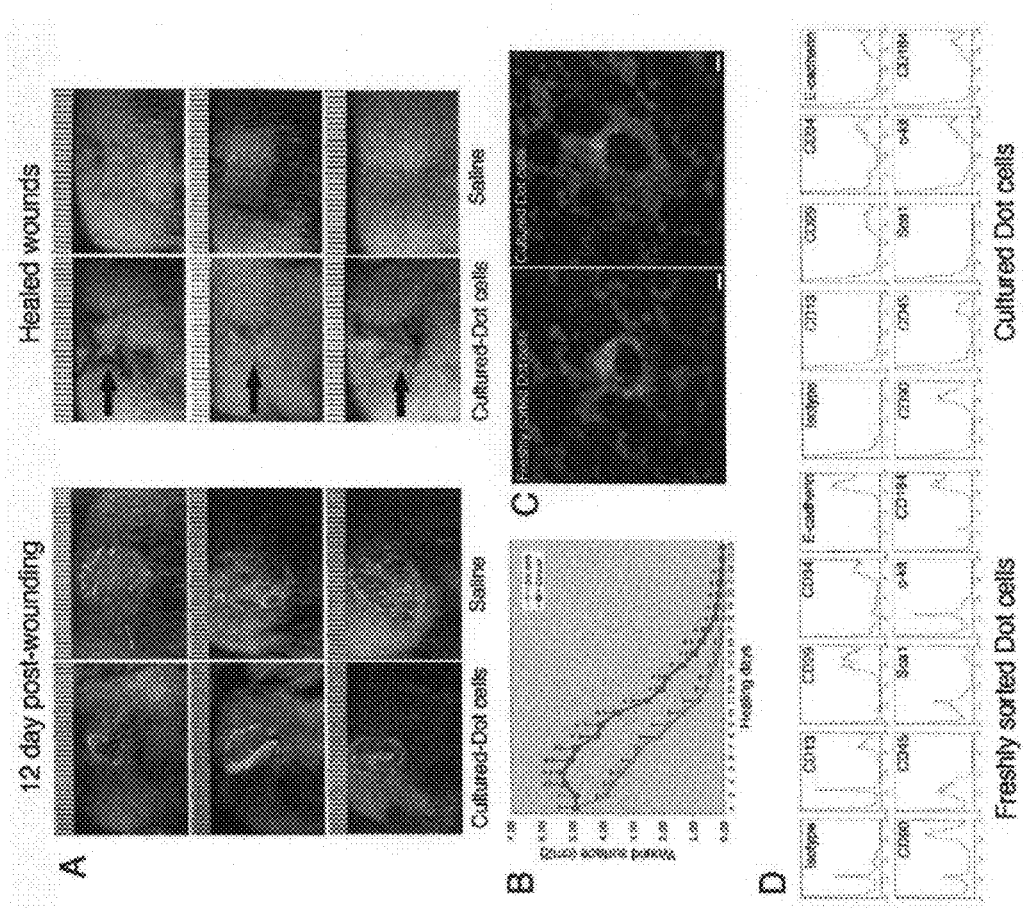
FIG. 14. In vitro expanded blood Dot cells accelerate wound healing in diabetic mice. A 0.5 cm2 size open wound was created on the dorsal skin of each diabetic mouse before 1.5 million cultured Dot cells were transplanted through tail-vein injection. The control group received saline. Three mice were used for each group. (A) 12-day and 24 day healed wounds on Dot cell-transplanted and control diabetic mice. Newly grown hairs (arrows) surrounded the scar of each Dot cell-transplanted mouse. (B) Quantitative analysis of wound areas during healing. Accelerated healing was observed in Dot cell transplanted diabetic mice by the third day after wounding. Each number was calculated as mean±SD (N=3). Student t-test, non-paired, two-tailed statistic analysis was used. (*=P δ 0.05). (C) In vitro expanded or freshly sorted blood-derived GFP-labeled Dot cells show similar regenerative effects during wound healing. Dermal GFP-labeled cells were expressed in the wound bed in a similar pattern after transplantation of one million cultured or freshly isolated Dot cells. (D) FACS analysis of the surface markers on either freshly sorted or in vitro expanded Dot cells. FACS analysis was repeated at least three times.

In vitro expanded Dot cells accelerate diabetic wound healing. Until now, BM cells used for transplantation were freshly sorted BM stem cells because in vitro expansion of BM stem cells diminishes their tissue regenerative activity. Therefore, the regenerative effects of cultured blood-derived Dot cells were examined during wound healing in diabetic mice. In vitro expanded adult mouse blood-derived Dot cells were hematogenously injected into wounded diabetic mice. FIG. 14A shows 12-day unhealed wounds, and healed wounds on Dot cell-transplanted and control mice. Significantly accelerated healing occurs in Dot cell-transplanted mice. The scar tissue in the Dot cell-transplanted mice was significantly smaller compared to the control group.

In addition, newly grown hair (arrows in healed wounds) was observed at the scar periphery of Dot cell-transplanted mice. Cultured Dot cells not only reduce scar, but also increase reepithelialization and hair growth. Wound areas were measured every one or two days until complete healing occurred. Quantitative wound size analysis confirmed that significantly accelerated healing occurs in Dot cell-transplanted diabetic mice by the third day after wounding (FIG. 14B). The effects of cultured GFP-labeled Dot cells on postnatal wound repair were examined in Balb/C mice. The regenerated wound tissue after cultured Dot cell treatment shows a similar structure as that of freshly sorted Dot cells in Example 1. FIG. 14C shows wound regenerative activities of freshly sorted and in vitro expanded Dot cells. GFP-expressing dermal cells appear at the wound bed after transplantation of cultured GFP-labeled Dot cells, which is similar to that of the freshly sorted GFP-labeled Dot cells. FIG. 14D shows FACS analysis of surface markers on either freshly sorted blood-derived Dot cells or the in vitro expanded Dot cells. Freshly sorted Dot cells express E-cadherin, integrin β1/CD29, CXCR4/CD184, CD90 and CD34. Only a small amount of freshly sorted Dot cells express Sca1. However, after one month in culture, the number of Dot cells that express E-cadherin, integrin β1 and CD184 is significantly reduced, and the number that express CD90 and CD34 remains the same. Interestingly, a significant amount of Dot cells start to express c-kit and CD45, but none express Sca1. The change of surface markers may correlate with the increased variety of Dot cell shapes in culture (FIG. 10B). Culture conditions create a mixed population of Dot cells with different surface marker expression patterns.

Figure 15:
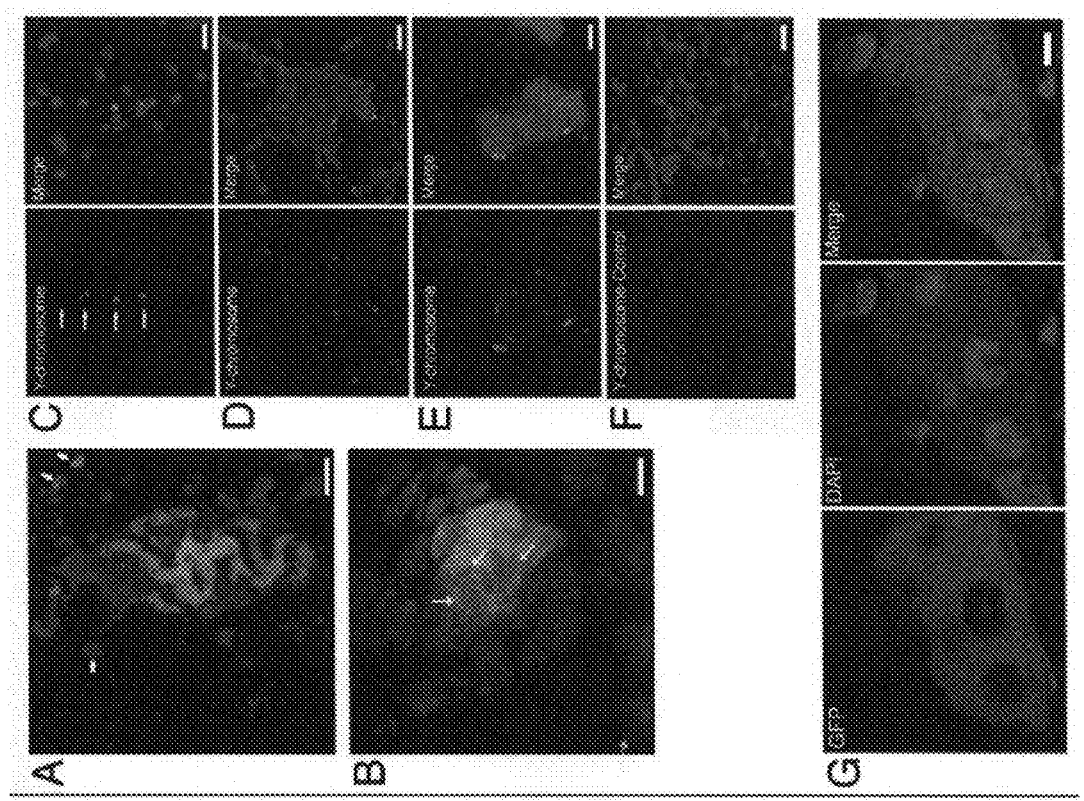
FIG. 15. Fused Dot cells are released from spheroids in the wound bed after Dot cell transplantation. One million male Dot cells were collected from the blood of either male mice or GFP-transgenic mice and transplanted into each wounded female adult wild-type mouse via tail-vein injection. (A) A merged confocal microscopic image of a 3-day wound section after male Dot cell-transplantation. A large spheroid-like structure composed of crowded y-chromosome-positive small cells is located close to the open wound edge. Some grouped Dot cells (thick arrows) are also near this spheroid. (B) A confocal merged image of a GFP-expressing spheroid in the wound. Grouped cells are either embedded within or emerging from this spheroid. (C) Four of the dermal cells express multiple y-chromosomes in a 3-day wound section (arrows). (D) Almost every cell expresses multiple y-chromosomes in the unrepaired wound bed of a 5-day wound section. (E) Higher confocal magnification shows multiple y-chromosomes expressed as single dots in the nuclear area of a dermal cell. (F). No y-chromosomes are expressed in the control wound. (G) Confocal images of a 5-day wound section after GFP-labeled Dot cell-transplantation. The images show a large GFP-positive spheroid with grouped small cells on its surface. The spheroid stained positive, but weakly, to DAPI compared to the grouped cells within it. Bar in 6A=20 μm; in 6B=10 μm; bars in 6C, 6D and 6F=20 μm; bar in 6E=3 μm. Bar in 6F=5 μm.

Fused Dot cells are released from spheroids in the wound bed. Cultured blood-derived Dot cells form large spheroids in vitro, and groups of fused Dot cells are released from the spheroids (FIG. 10D). The fusion-differentiation of Dot cells was examined in vivo. Y-chromosome and GFP expression were used as Dot cell markers after tail vein injection into wounded mice. Both male and GFP-labeled Dot cells formed into spheroids. The morphology of these large spheroids was similar to that of the spheroids we observed in vitro, suggesting that Dot cells form into spheroids after transplantation in vivo. In FIG. 15A, a large spheroid composed of numerous nuclear particles and y-chromosomes (red) is located near the wound bed. Numerous small DAPI-positive particles, each with a positive y-chromosome stain, are located close to this spheroid. In addition, fused DAPI-positive particles with multiple y-chromosomes (arrows) are released from the spheroids and migrate to the wound bed.

FIG. 15B shows a spheroid with GFP expression near the wound bed. Several nuclei are embedded in this spheroid, suggesting they are derived through Dot cell fusion. FIG. 6C shows four nuclei (arrows), which express multiple-y-chromosomes in a linear arrangement in the wound bed, suggesting they had migrated along the same path. The adjacent DAPI positive nuclei do not show expression of y-chromosomes. FIG. 15D shows an area of unhealed dermal tissue from a 5-day wound section. Almost every cell expresses multiple y-chromosomes, indicating the regeneration of majority dermal cell occurs through transplanted male Dot cell fusion. Individual y-chromosomes are indistinguishable with a 100× lens, but after adding 8× zoom, y-chromosomes are seen as individual dots in the nuclear area (FIG. 15E). FIG. 15G shows confocal images of a 5-day wound section after GFP-labeled Dot cell-transplantation. The large GFP-positive spheroid has hollow areas inside its structure, which coincides with the large nuclei in the spheroids shown by DAPI staining. The spheroid has weaker DAPI staining compared to that of these large nuclei, suggesting the nuclear material of Dot cells is less dense than the fused cells. Combining these data with those in FIG. 14 that show transplanted Dot cells also increase wound reepithelialization, we conclude that in vitro expanded Dot cells undergo self fusion-differentiation and become either dermal or epidermal cells. Transplanted Dot cells contribute to most of the new tissue regenerated during wound healing.

Dot cell fusion, followed by transdifferentiation, occurs under physiological conditions. We found that transplanted Dot cells repair wounds by fusion. However, whether Dot cell fusion events occur under physiological conditions is not known. Wounds from saline injected female virgin mice were examined for the fusion of Dot cells. Single dermal cells expressing multiple x-chromosomes were found in the wound area and along blood vessels. The appearance of fused cells occurs at low frequency, suggesting a low number of Dot cells are present in the wounds. In confocal images of a wound section at lower magnification, multiple x-chromosomes are seen in one nucleus, however a few x-chromosomes are also observed in other nuclei. These data suggest that these multiple x-chromosome expressing cells migrated along a blood vessel. Multiple x-chromosomes appeared as individual dots in two nuclei, suggesting these cells are derived from fused Dot cells. No spheroid structures were found in the control wounds after saline injection, suggesting that under physiological conditions, the fused Dot cells in the wounds likely originated from the bone marrow but at a low frequency.

Our results also demonstrate that the frequency of fusion is dependent on the number of Dot cells, i.e. a higher number of Dot cells induces a higher frequency of self-fusion. When more Dot cells are in the circulation, wounds are regenerated mainly by Dot cell fusion differentiation. In addition, although we demonstrate that Dot cell self-fusion occurs in vivo during tissue repair, we do not exclude the possibility that Dot cells also fuse to the local dermal cells, i.e. Dot cell-target cell fusion, albeit in low frequency. Both our in vitro and in vivo data strongly support that blood derived Dot cells become differentiated cells through aggregation and self-fusion differentiation. Our data also provide evidence that in vitro-expanded, blood-derived, Dot cells have a strong regenerative activity after transplantation.

Dot cells express stem cell transcription factors and their lineage differentiation is determined by the microenvironment where they are located. Dot cells may be a mixed population, and they perform self-renewal though a non-division mechanism. We believe that Dot cells are more primitive than MSCs, and may be the true circulating stem cells. Dot cells are a useful therapeutic modality for clinical treatment of injured tissues. Because culture expanded Dot cells have similar repair effects to freshly sorted Dot cells, the amount of blood needed for isolation of Dot cells for future clinical application will be reduced. Moreover, postnatal blood-derived Dot cells have a regenerative function.

Material and Methods

Animals and materials. Four-week-old male, 8 to 10 weeks old female Balb/C mice, GFP (FVB.Cg-Tg(ACTB-EGFP) B5Nagy/J, Jackson Lab) mice and diabetic (B6.Cg-m+/+ Leprdb/J, Jackson lab) mice were bred or maintained in the Stanford Animal Care Laboratory. Mice received food and water ad libitum. All procedures with animals were conducted in accordance with university-approved protocols according to NIH guidelines. E-cadherin and FGF-2 antibodies were from Santa Cruz biotechnology (Santa Cruz, Calif.). Alexa Fluor goat anti-rabbit IgG was from Molecular Probes (Eugene, Oreg.). Rhodamine-labeled y-chromosome and FITC-labeled x-chromosome probes were from ID Labs (Ontario, Canada). Anti-rabbit IgG-conjugated magnetic beads and mini columns were from Miltenyi Biotech Inc. (Auburn, Calif.).

Dot cell isolation and in vitro expansion. Blood collected from 4-week old male mice through cardiac puncture was diluted with PBS before passing through a cell strainer and followed by incubation in red blood cell lysis buffer. Magnetic bead cell sorting was followed per manufacturer's instructions. Sorted E-cadherin positive cells were cultured on collagen coated plates in α-MEM containing 20% FBS and antibiotics in a 5% $CO_2$ humid incubator at 37° C. After cell colonies reached sub-confluence, cells were trypsinized and passaged to fresh collagen coated plates.

Wound creation and cell transplantation. For diabetic wound healing, one 1.5 cm$^2$ wound was created on the dorsal skin of each diabetic mouse. One and half million of cultured Dot cells were then transplanted through tail vein to each wounded diabetic mouse. Three mice were used in each group. The control group was received saline through of tail-vein. Eight to ten week-old female Balb/C mice were anesthetized. Two 0.6 cm diameter excisional wounds were made with a biopsy punch on dorsal skin. One million cultured GFP-labeled Dot cells or Dot cell from male Balb/C mice in 100 μl normal saline were then injected with 26-gauge needle through tail-vein in each wounded mouse.

Fluorescent in situ hybridization (FISH). The method for FISH labeling was performed according to the manufacturer's instructions. Briefly, wounds were collected from female mice that were transplanted with male Dot cells. Ten μm frozen wound sections were washed and digested with pepsin. After dehydration, rhodamine-labeled y-chromosome or FITC-labeled x-chromosome probes were added to each section and denatured at 75° C. for 10 min before hybridization at 37° C. over night in the dark. After washing, sections were stained with DAPI for cell nuclear localization. The locations of chromosome labeled cells were determined by a confocal microscopy. The control wounds were collected from female mice injected with saline.

Immunofluorescent staining. For fluorescent studies, cultured Dot cells were fixed, washed, blocked and then reacted with different antibodies at dilutions ranging between 1:50 and 1:200 in blocking buffer over night at 4° C. Cells were then washed, and reacted with a fluorescent conjugated secondary antibody for 1 hour. After washing, cells were counterstained with DAPI and photographed by confocal microscopy (Leica DM IRE2). The control group was treated without primary antibody. The scanned confocal images were further analyzed with a software Velocity for 3 dimension and 360-degree rotation movie images.

Electron microscopy. Dot cells were fixed in 2% glutaraldehyde and 4% paraformadehyde in sodium cacodylate buffer, pH 7.3, for 30 min at room temperature. After washing with in sodium cacodylate buffer, ice cold, 1% osmium tetroxide in distilled water was added to the cell pellet, followed with gentle shaking at 4° C. for 2 hours. After washing with water, 1% uranyl acetate was added to the cell pellet overnight. Cells were then dehydrated with serial ethanol dilutions and embedded in Epon at 65° C. for 24 hours. Ultra-thin sections were cut and doubly stained with uranyl acetate and lead citrate followed by electron microscopy examination.

Fluorescent cell sorting (FACS). Dot cells from either freshly sorted or collected from culture conditions were washed with PBS and blocked with 1% normal horse serum (NHS) for one hour. Then, cells were labeled with different antibodies in the dilution from 1:50 or 1:100 in 100 μl PBS with 1% NHS for 30 min and followed with washes in PBS with 1% NHS and reacted with secondary antibody conjugated with either FITC (fluorescein isothiocyanate) or PE for 30 min on ice. After washing, the ratio of positive labeling was analyzed using the LSR FACS machines at the Stanford Shared FACS Facility. Flow cytometry data was then acquired with CellQuest software (BD Biosciences) and analyzed with FlowJo software (FlowJo, Palo Alto, Calif.). Isotope antibody labeled cells was used for non-specific labeling control.

Example 3

Dot Cell Differentiation

Figure 16:
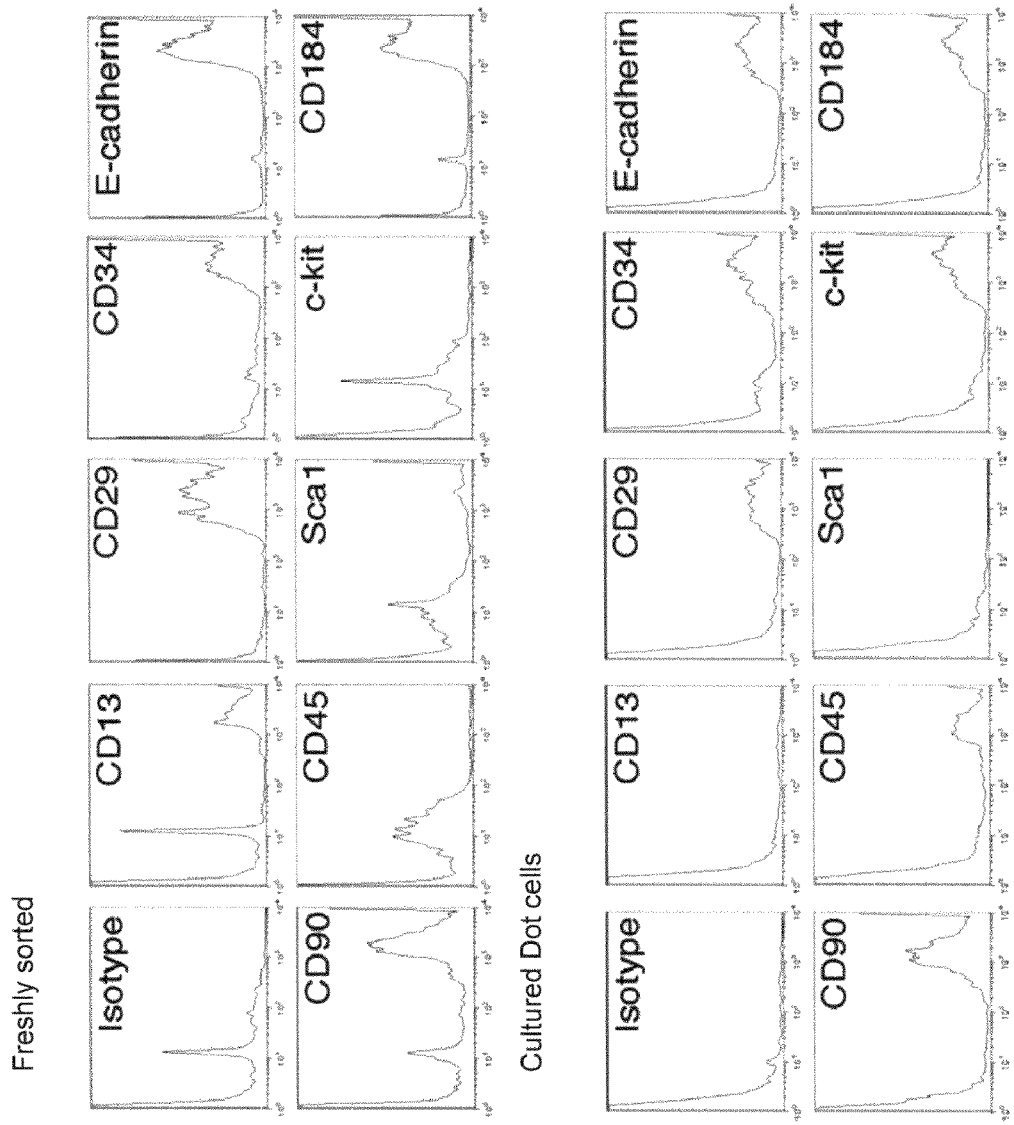
FIG. 16. FACS analysis of surface markers on either freshly sorted blood-derived Dot cells or the in vitro expanded Dot cells.

FIG. 16 shows FACS analysis of surface markers on either freshly sorted blood-derived Dot cells or the in vitro expanded Dot cells. Freshly sorted Dot cells express E-cadherin, integrin β1/CD29, CXCR4/CD184, CD90 and CD34. Only a small amount of freshly sorted Dot cells express Sca1. However, after one month in culture, the number of Dot cells that express E-cadherin, integrin β1 and CD184 is significantly reduced, and the number that expresses CD90 and CD34 remains the same. Interestingly, a significant amount of Dot cells start to express c-kit and CD45, but none express Sca1. The change of surface markers may correlate with the increased variety of Dot cell shapes in culture.

Figure 17:
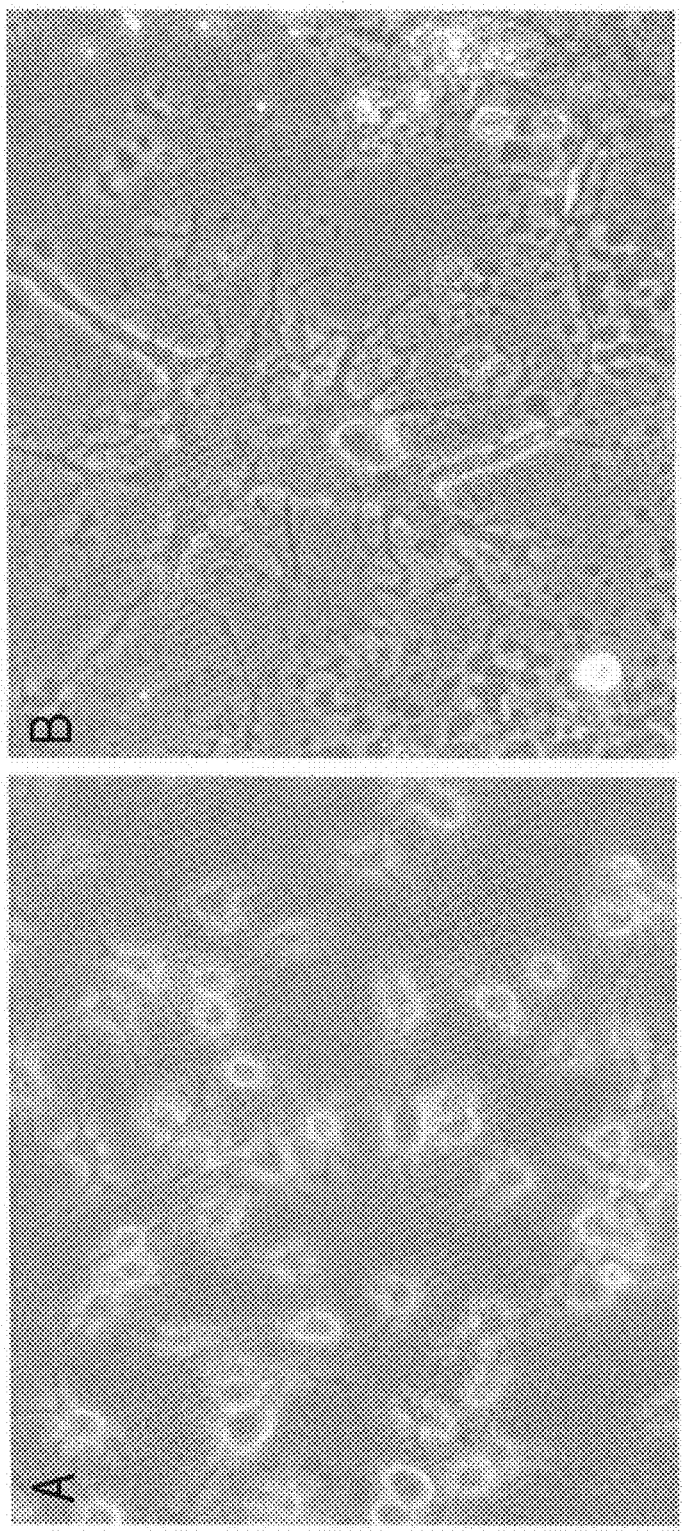
FIG. 17. Dot cells differentiate into neuron-like cells in vitro (A-B).

As shown in FIG. 17, Dot cells differentiate into neuron-like cells in vitro. Dot cells were cultured and they have spontaneous differentiation. FIG. 17A shows the morphology of glial cells. 17B shows that Dot cells differentiate into a neuron-like morphology.

Figure 18:
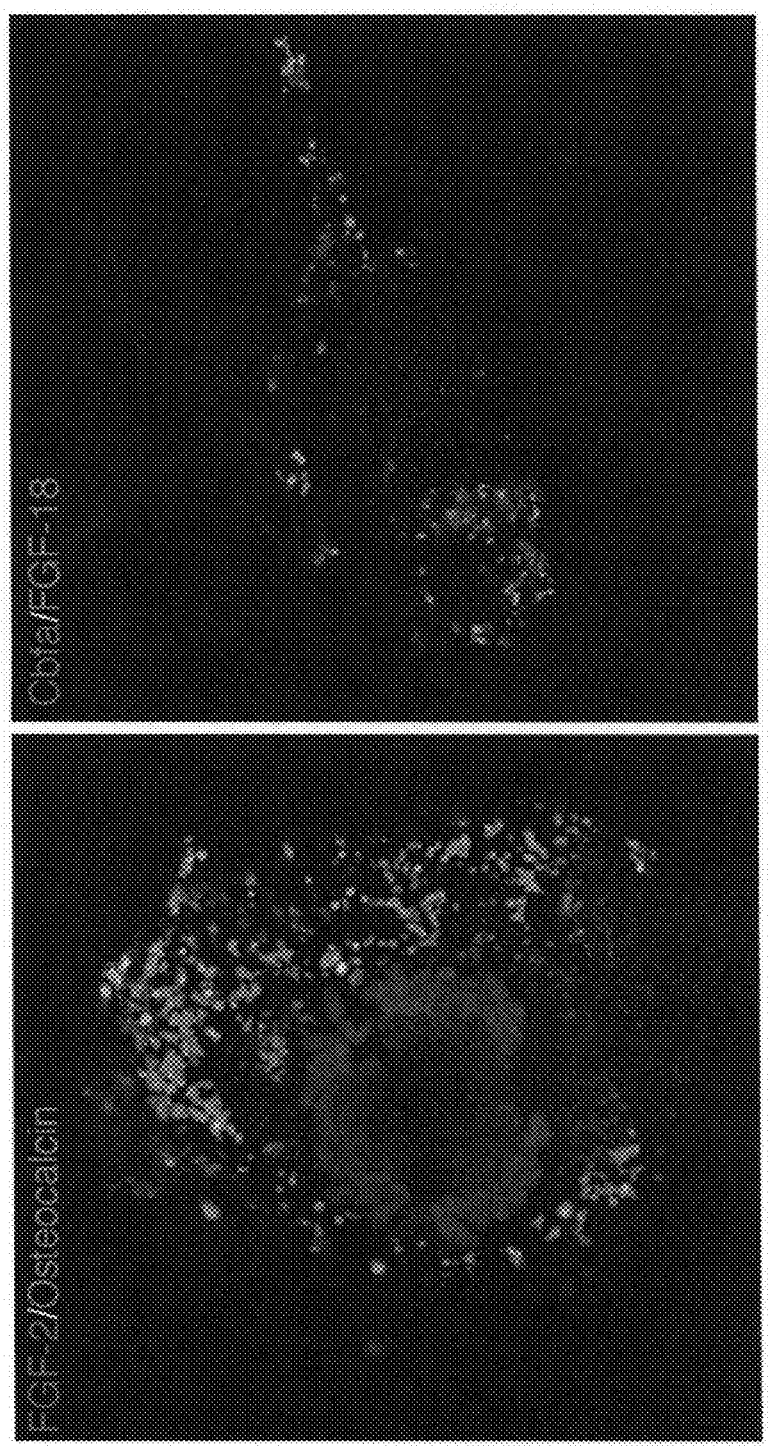
FIG. 18. Dot cells differentiate into osteoblasts in vitro.

Shown in FIG. 18, Dot cells differentiate into osteoblasts in vitro. Dot cells were co-cultured with MC3T3 cells (osteoblast cell line). After 7 days, the co-cultured cells were fixed and the osteoblasts specific markers were stained for the bone differentiation of Dot cells. Dot cells differentiate into osteoblasts by self-fusion. Cbfa/Runx-2 is the early marker of osteoblasts differentiation, and osteocalcin is the marker for differentiated osteoblasts.

Figure 19:
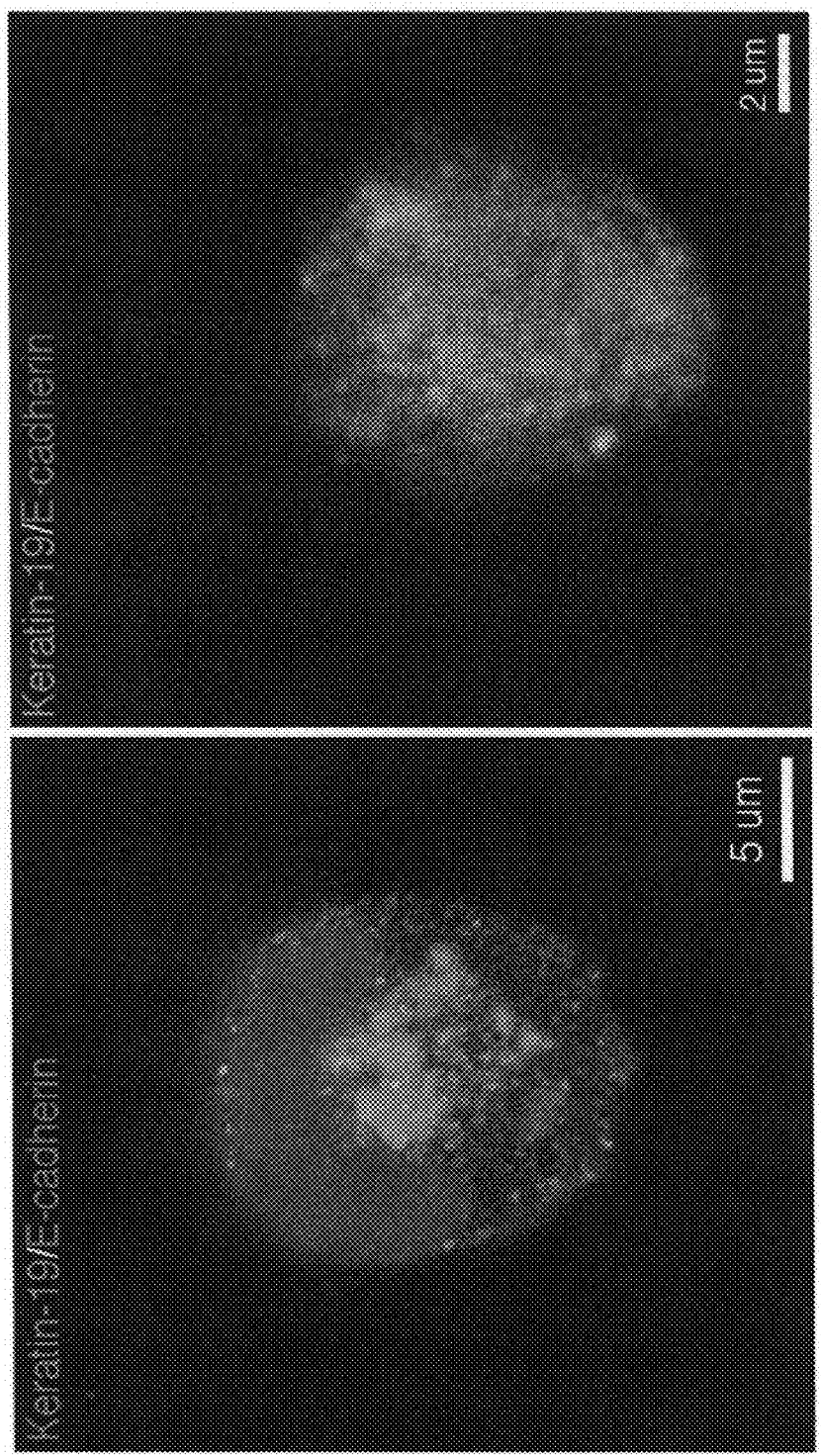
FIG. 19. Dot cells differentiate into keratinocytes in vitro.

FIG. 19. Dot cells differentiate into keratinocytes in vitro. Dot cells were co-cultured with epithelial cells and after 7 to 10 days, cells were fixed and the epithelia cell marker expression of Dot cells was examined using immunofluorescent methods. Specific marker keratin-19 and E-cadherin are expressed on these tiny cells. The one on the right does not have clear nucleus but it dose express both E-cadherin and keartin-19. The cell on the left has clear nuclear structure but with E-cadherin expression inside of the cell, suggesting this cell is during the transition of differentiation.

Figure 20:
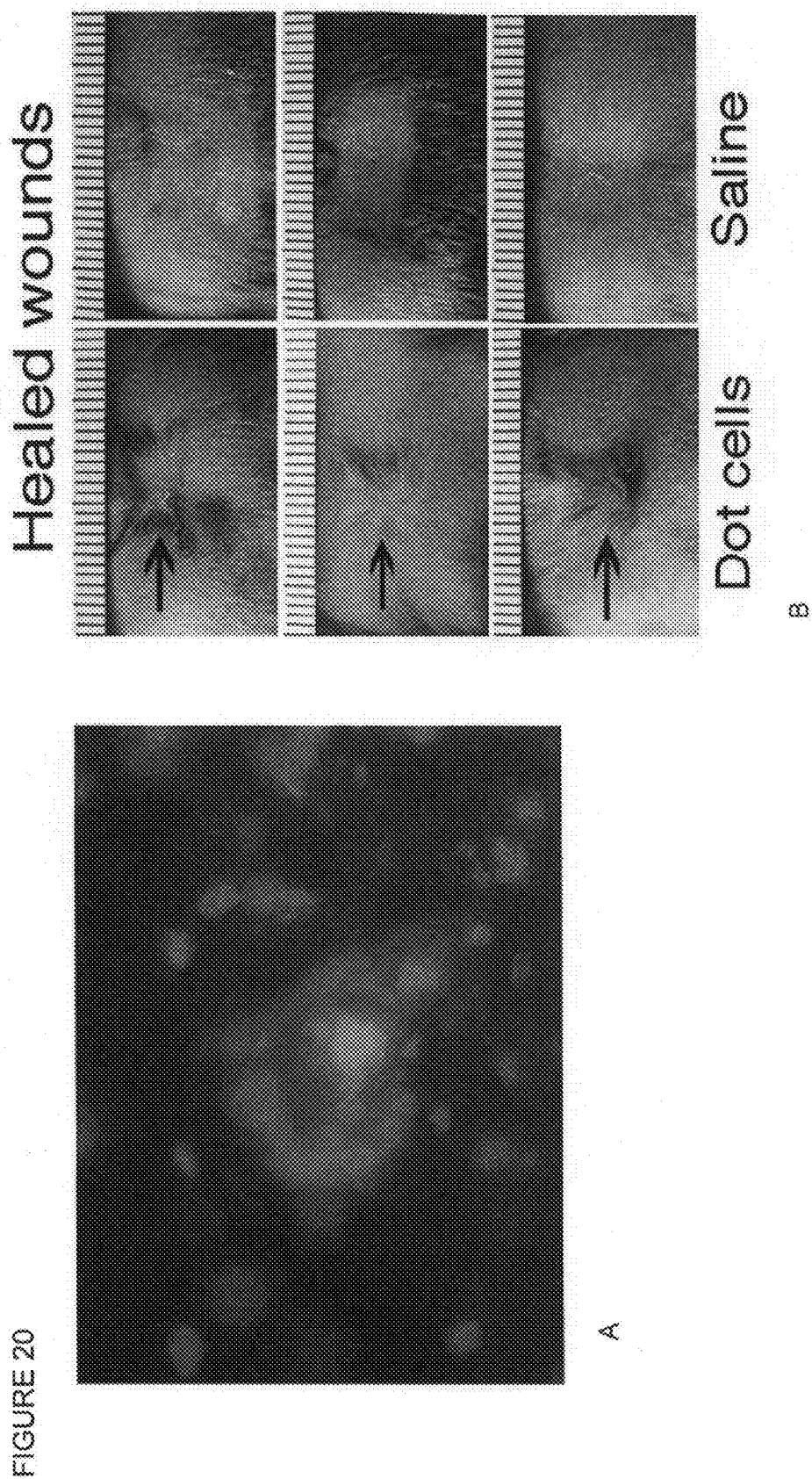
FIG. 20. Dot cells differentiate into keratinocytes in vivo (A-B).

Shown in FIG. 20, Dot cells differentiate into keratinocytes in vivo. The differentiation of Dot cells to keratinocytes was also examined in vivo. GFP-labeled Dot cells were transplanted to skin wound Balb/C mice via tail-vein injection. Wounds were collected and GFP labeled hair follicles were examined using a fluorescent microscopy. FIG. 20A shows a group of GFP-labeled cells forming a hair follicle. A 1.5 cm$^2$ size open wound was created on the dorsal skin of each diabetic mouse before 1.5 million cultured Dot cells were transplanted through tail-vein injection. The control group received saline. Three mice were used for each group. FIG. 20B shows the healed wounds on Dot cell-transplanted and control diabetic mice. Newly grown hairs (arrows) surrounded the scar of each Dot cell-transplanted mouse.

Figure 21:
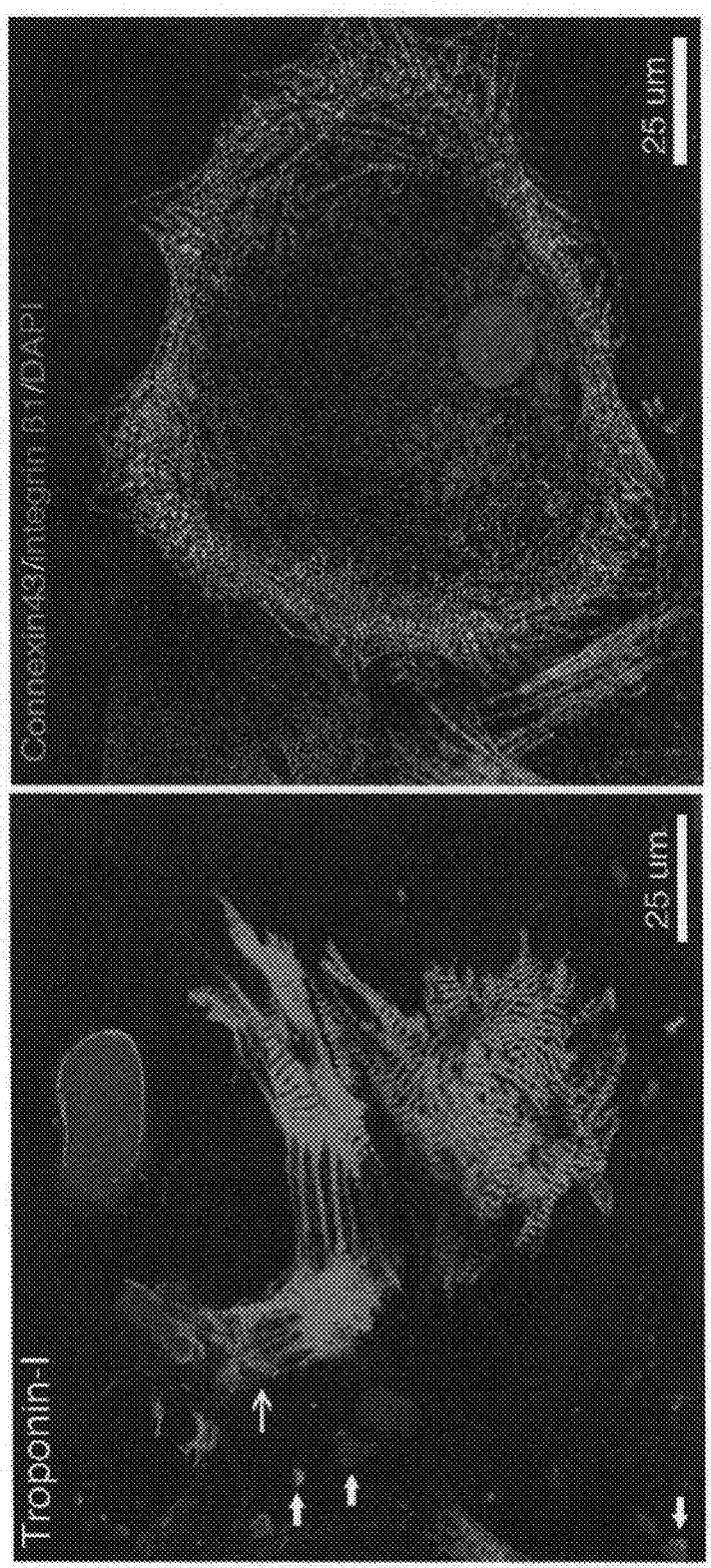
FIG. 21. Dot cells differentiate into cardiomyocytes in vitro.

As shown in FIG. 21, Dot cells differentiate into cardiomyocytes in vitro. Cardiomyocytes were isolated from the hearts of E18 fetal mice, and then were cultured on culture plates. Dot cells were added to cardiomyocytes after 24 hours.

After 7 to 10 days, the expression of cardiomyocytes specific markers, troponin-I and connexin-43, was examined on the co-cultured Dot cells. Troponin-I was expressed on very small cells (arrows), suggesting Dot cells initiate the expression of troponin-I before they differentiate to cardiomyocytes. However, connexin-43 expressed only on the differentiate cardiomyocytes, suggesting this that Dot cells acquire this marker after the differentiation. Integrin β1 is expressed inside this cell and some small DAPI-positive particles are also located inside, these indicate that this cell is derived by Dot cell self-fusion.

Dot cells also differentiate to cardiomyocytes that contract. GFP-labeled Dot cells were cultured in a lower chamber, and cardiomyocytes were cultured in the upper chamber of a co-culture chamber environment. A control group was cardiomyocytes on the upper chamber only. After 20 days, grouped cells were seen on the upper chamber. No contractile cells were seen in the control group after 20 days in culture. However, the cardiomyocytes that co-cultured with Dot cells constantly contracted, and become a large muscular fiber structure. After 4 month in culture, the muscular structure still contract and most of these contracting cells are GFP-labeled, indicating DOT cell lineage.

Dot cells differentiate into cardiomyocytes in vivo. Acute myocardial infarction was made by left anterior descending artery (LAD) ligation on 10-weeks old Balb/C mice. GFP-labeled Dot cells were then transplanted to the mice within one hour after the surgery. After 4 weeks the mouse was sacrificed and heart was collected. The GFP-expressing cells were examined on the heart using a fluorescent microscopy. GFP-positive cardiomyocytes were located in the heart muscle fiber, especially between the myofibers.

Figure 22:
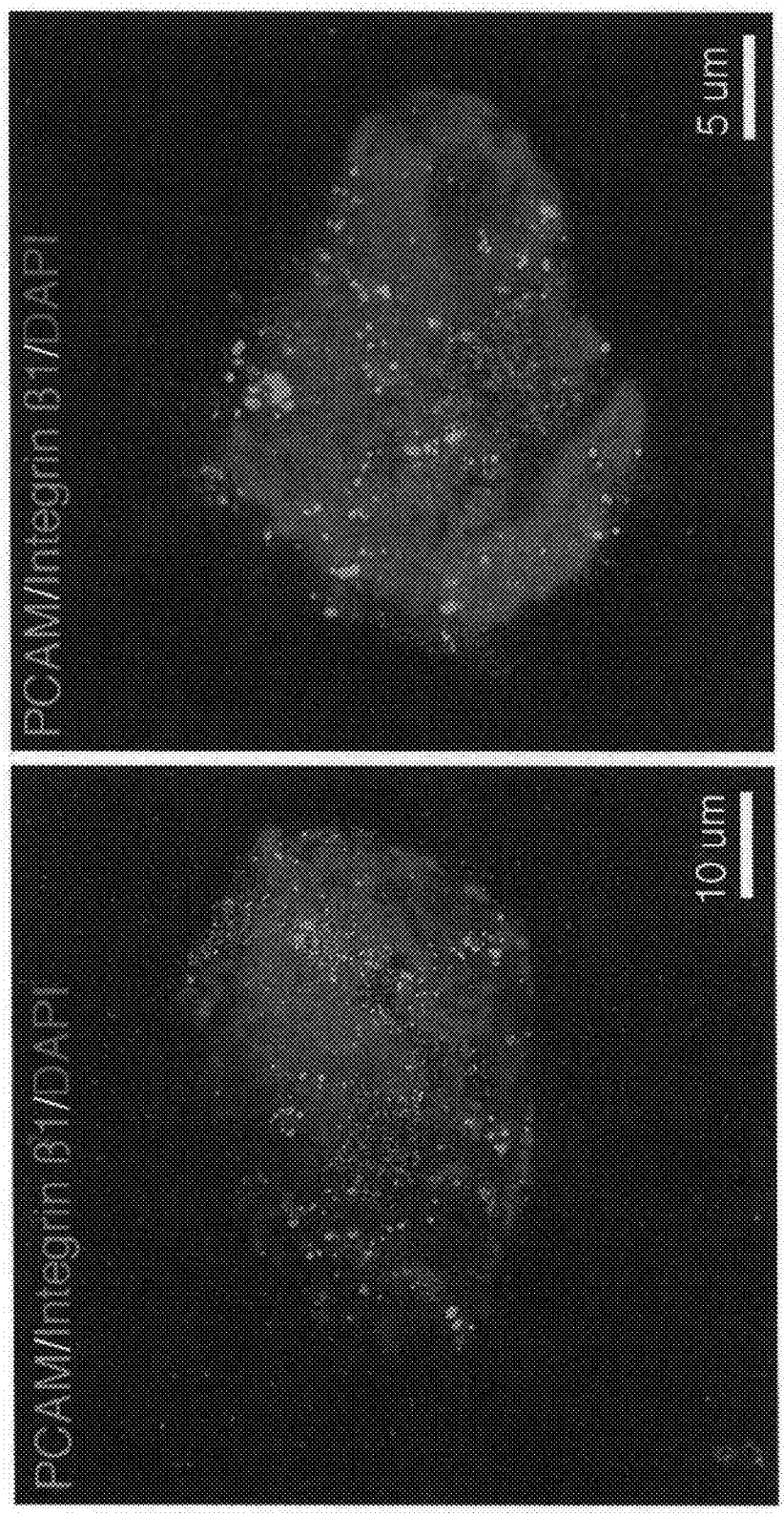
FIG. 22. Dot cells differentiate into endothelial cells.

Dot cells differentiate into endothelial cells in vitro and in vivo. Dot cells were co-cultured with endothelial cells and the expression of PECAM, the endothelial specific marker was examined after 7 to 10 days in co-culture. FIG. 22 shows two Dot cell-self-fusion derived cells, both express integrin β1 and PECAM after the co-culture. In vivo, GFP-labeled Dot cells were transplanted into wounded Balb/C mice and after 3 days wounds were examined. A GFP-labeled vascular structure was found in the wound area.

Figure 23:
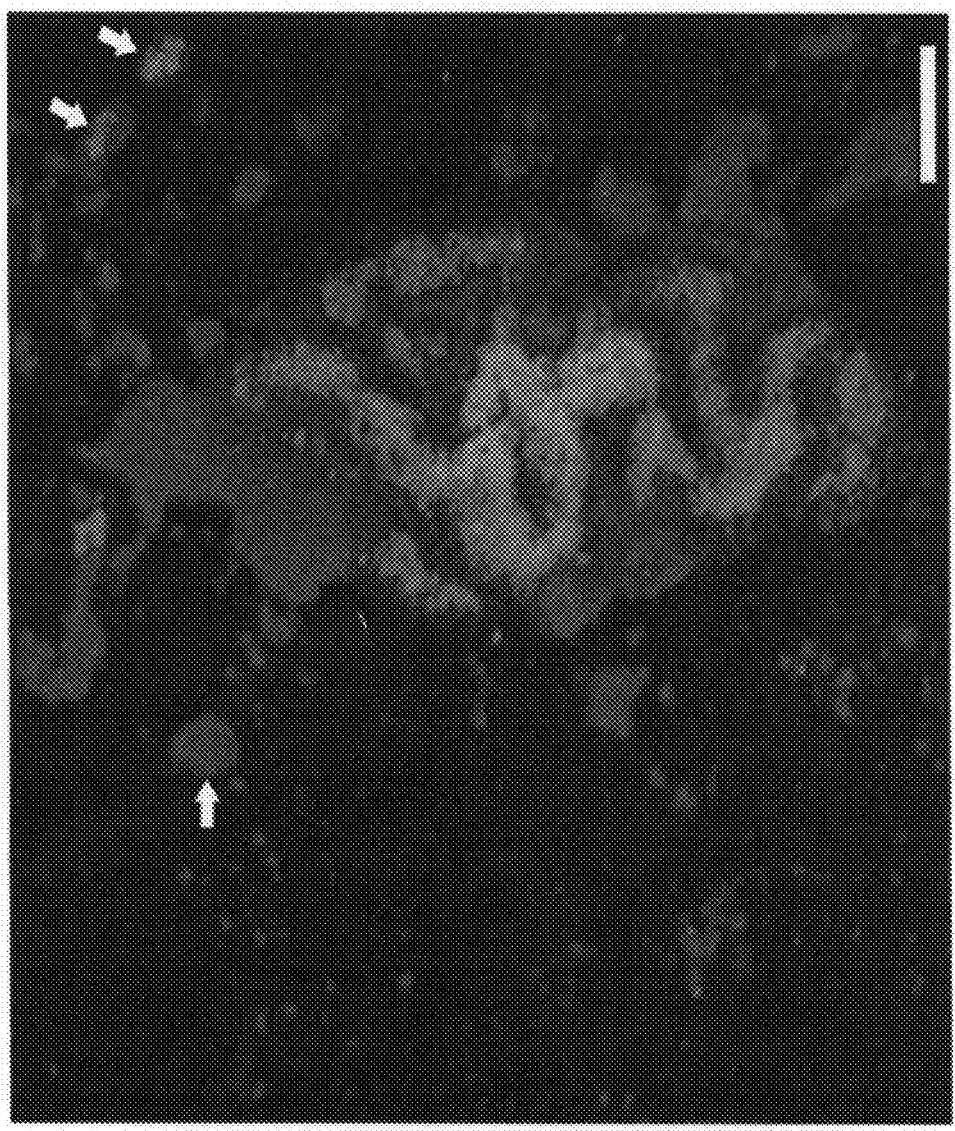
FIG. 23. Dot cell in vivo differentiation is also by self-fusion.

Shown in FIG. 23, Dot cell in vivo, differentiation is also by self-fusion. Male Dot cells or GFP-labeled Dot cells were transplanted via tail vein to either female adult mice or wild-type mice. FIG. 23 shows a merged confocal microscopic image of a 3-day wound section after male Dot cell-transplantation. A large spheroid-like structure composed of crowded y-chromosome-positive small cells is located close to the open wound edge. Some grouped Dot cells are also near this spheroid.

Transplantation of Dot cells does not induce rejection. Dot cells that were isolated from GFP-transgenic mice were transplanted to Balb/C mice, and from Balb/C mice to diabetic mice. These are different strains of mice. Dot cells did not rejected or destroyed by host, instead, Dot cells retained their functions on tissue regeneration.

What is claimed is:

1. A composition of isolated mammalian Dot cells, wherein at least 95% of the cells in said composition are E-cadherin$^+$, integrin β1$^+$, CD90$^+$, CXCR4$^+$ Dot cells from 0.1-2 μM in diameter;
   wherein the Dot cells can contribute in vivo to tissue regeneration.

2. The composition of mammalian cells according to claim 1, wherein said cells are isolated from blood or bone marrow.

3. The composition of mammalian cells according to claim 1, wherein said cells are isolated from dermal tissue.

4. The composition of mammalian cells according to claim 1, wherein said cells are isolated from human or mouse tissue.

5. The composition of mammalian cells according to claim 1, wherein said cells are isolated from fetal tissue.

6. The composition of mammalian cells according to claim 1, wherein said cells are isolated from adult tissue.

7. The composition of mammalian cells according to claim 1, wherein said cells are isolated from blood or bone marrow.

8. The composition of mammalian cells according to claim 1, wherein the cells are freshly isolated from a mammalian donor.

9. The composition of mammalian cells according to claim 1, wherein the cells are frozen.

* * * * *